United States Patent
Bukesov et al.

(10) Patent No.: US 12,023,097 B2
(45) Date of Patent: Jul. 2, 2024

(54) SELECTIVE LASER FIRING FOR TISSUE SAFETY

(71) Applicant: GYRUS ACMI, INC., Southborough, MA (US)

(72) Inventors: Sergey A. Bukesov, Acton, MA (US); Rachel D. Schnakenberg, Minneapolis, MN (US); Kurt G. Shelton, Bedford, MA (US); Brian M. Talbot, Southborough, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 217 days.

(21) Appl. No.: 16/984,414

(22) Filed: Aug. 4, 2020

(65) Prior Publication Data

US 2021/0038304 A1 Feb. 11, 2021

Related U.S. Application Data

(60) Provisional application No. 63/017,450, filed on Apr. 29, 2020, provisional application No. 62/882,837, filed on Aug. 5, 2019.

(51) Int. Cl.
*A61B 18/20* (2006.01)
*A61B 1/00* (2006.01)
(Continued)

(52) U.S. Cl.
CPC ........ *A61B 18/26* (2013.01); *A61B 1/000094* (2022.02); *A61B 1/0655* (2022.02);
(Continued)

(58) Field of Classification Search
CPC ....... A61B 18/20; A61B 18/24; A61B 18/245; A61B 18/26; A61B 2018/263; A61B 2018/266; A61B 5/0075
See application file for complete search history.

(56) References Cited

U.S. PATENT DOCUMENTS 5,820,627 A 10/1998 Rosen et al.
5,873,875 A 2/1999 Altshuler
(Continued)

FOREIGN PATENT DOCUMENTS

CN 104619281 A 5/2015
CN 105377108 A 3/2016
(Continued)

OTHER PUBLICATIONS

"International Application Serial No. PCT/US2020/044867, International Search Report mailed Nov. 12, 2020", 6 pgs.
(Continued)

*Primary Examiner* — Lynsey C Eiseman
(74) *Attorney, Agent, or Firm* — Schwegman Lundberg & Woessner. P.A.

(57) ABSTRACT

Systems, devices, and methods for identifying different structure types with distinct composition in vivo and adjusting surgical laser output accordingly in a medical procedure are disclosed. An exemplary laser treatment system comprises a laser system configured to generate a laser beam for delivery to a target in a body, and a controller circuit configured to receive a signal reflected from the target in response to electromagnetic radiation produced by a light source, and generate one or more spectroscopic properties from the reflected signal. The controller circuit can identify the target as one of a plurality of structure types, such as tissue types or calculi types with respective compositions, using the one or more spectroscopic properties. The laser system can be controlled to operate in an operating mode based on the target identification.

36 Claims, 12 Drawing Sheets

(51) Int. Cl.
  *A61B 1/06* (2006.01)
  *A61B 18/26* (2006.01)
  *A61B 18/00* (2006.01)
  *A61B 18/22* (2006.01)

(52) U.S. Cl.
  CPC .... *A61B 18/20* (2013.01); *A61B 2018/00696* (2013.01); *A61B 2018/00982* (2013.01); *A61B 2018/2015* (2013.01); *A61B 2018/2065* (2013.01); *A61B 2018/2272* (2013.01)

(56) References Cited

U.S. PATENT DOCUMENTS

| | | | |
|---|---|---|---|
| 6,554,824 | B2 | 4/2003 | Davenport et al. |
| 9,017,316 | B2 | 4/2015 | Khatchaturov et al. |
| 9,445,871 | B2 | 9/2016 | Kang et al. |
| 9,486,286 | B2 | 11/2016 | Hodel et al. |
| 9,757,199 | B2 | 9/2017 | Chia et al. |
| 9,949,615 | B2 | 4/2018 | Zappia et al. |
| 9,968,403 | B2 | 5/2018 | Hasenberg et al. |
| 10,039,604 | B2 | 8/2018 | Chia et al. |
| 10,067,304 | B2 | 9/2018 | Yu et al. |
| 10,105,184 | B2 | 10/2018 | Beck et al. |
| 10,175,435 | B2 | 1/2019 | Peng et al. |
| 10,258,415 | B2 | 4/2019 | Harrah et al. |
| 10,383,690 | B2 | 8/2019 | Hodel et al. |
| 2002/0045832 | A1 | 4/2002 | Giller et al. |
| 2003/0191398 | A1* | 10/2003 | Motz .............. A61B 5/0091 600/478 |
| 2008/0125634 | A1* | 5/2008 | Ryan .............. A61B 5/145 606/15 |
| 2009/0156900 | A1 | 6/2009 | Robertson |
| 2014/0005553 | A1* | 1/2014 | Ryan .............. A61B 5/02007 600/473 |
| 2014/0276101 | A1 | 9/2014 | Asselin et al. |
| 2015/0018807 | A1* | 1/2015 | Kircher .............. A61B 18/02 606/12 |
| 2015/0224249 | A1 | 8/2015 | Ciulla et al. |
| 2015/0230864 | A1 | 8/2015 | Xuan et al. |
| 2015/0272674 | A1 | 10/2015 | Xuan et al. |
| 2015/0289937 | A1* | 10/2015 | Chia .............. A61B 5/20 606/2.5 |
| 2016/0081749 | A1 | 3/2016 | Zhang et al. |
| 2016/0166319 | A1 | 6/2016 | Yu et al. |
| 2017/0173275 | A1* | 6/2017 | Anderson .......... A61B 5/0084 |
| 2017/0224420 | A1* | 8/2017 | Stringer .............. A61B 5/0059 |
| 2017/0325890 | A1 | 11/2017 | Chia et al. |
| 2018/0092693 | A1 | 4/2018 | Falkenstein et al. |
| 2019/0113700 | A1 | 4/2019 | Peng et al. |
| 2019/0151022 | A1 | 5/2019 | Yu et al. |
| 2019/0159839 | A1 | 5/2019 | Zhang et al. |
| 2019/0192237 | A1 | 6/2019 | Harrah et al. |
| 2019/0246908 | A1 | 8/2019 | Pyun et al. |
| 2019/0298449 | A1 | 10/2019 | Khachaturov et al. |
| 2019/0393669 | A1 | 12/2019 | Yu et al. |
| 2020/0264050 | A1* | 8/2020 | Auner .............. G01J 3/2803 |
| 2021/0128237 | A1 | 5/2021 | Bruno et al. |

FOREIGN PATENT DOCUMENTS

| | | |
|---|---|---|
| CN | 107743376 A | 2/2018 |
| CN | 114502091 A | 5/2022 |
| DE | 112020003749 T5 | 4/2022 |
| EP | 3510962 A1 | 7/2019 |
| EP | 3512448 A1 | 7/2019 |
| EP | 3522811 A1 | 8/2019 |
| JP | H02161937 | 6/1990 |
| JP | 2009213589 | 9/2009 |
| JP | 2013106692 A | 6/2013 |
| JP | 2018100955 A | 6/2018 |
| JP | 2018516705 | 6/2018 |
| JP | 2022544122 A | 10/2022 |
| WO | WO-1990014797 A1 | 12/1990 |
| WO | WO-2016201092 A1 | 12/2016 |
| WO | WO-2020033121 A1 | 2/2020 |
| WO | WO-2021026142 A1 | 2/2021 |

OTHER PUBLICATIONS

"International Application Serial No. PCT/US2020/044867, Written Opinion mailed Nov. 12, 2020", 6 pgs.

Bosschaart, Nienke, et al., "A literature review and novel theoretical approach on the optical properties of whole blood", Lasers Med Sci, (2014), 453-479.

Jacques, Steven, "Optical Absorption of Carbonized Tissue", [Online]. Retrieved from the Internet: <URL: https://omlc.org/spectra/carbon/>, (2018), 3 pgs.

Marafi, et al., "Laser spectroscopy and imaging of gallbladder stones, tissue and bile", Optics and Lasers in Engineering, Elsevier, Amsterdam, NL, vol. 45, No. 1, (Jan. 1, 2007), 191-197.

Vinnichenko, Victoriya, et al., "Comparison of a novel high-power blue diode laser ($\lambda$=442 nm) with Ho:YAG ($\lambda$=2100 nm), Tm fiber ($\lambda$=1940 nm), and KTP ($\lambda$=532 nm) lasers for soft tissue ablation", Proc. SPIE 10468, Therapeutics and Diagnostics in Urology, [Online]. Retrieved from the Internet: <URL: https://www.researchgate.net/publication/323002187>, (Feb. 2018), 8 pgs.

"Chinese Application Serial No. 202080064217.2, Voluntary Amendment filed Aug. 16, 2022", w/ English claims, 20 pgs.

"International Application Serial No. PCT/US2020/044867, International Preliminary Report on Patentability mailed Feb. 17, 2022", 8 pgs.

"Indian Application Serial No. 202247004151, First Examination Report mailed Oct. 17, 2022", 6 pgs.

"Japanese Application Serial No. 2022-507456, Notification of Reasons for Refusal mailed Mar. 14, 2023", w English Translation, 15 pgs.

"Indian Application Serial No. 202247004151, Response filed Apr. 13, 2023 to First Examination Report mailed Oct. 17, 2022", 36 pgs.

"Japanese Application Serial No. 2022-507456, Response filed Jun. 8, 2023 to Notification of Reasons for Refusal mailed Mar. 14, 2023", with English claims, 25 pgs.

"Japanese Application Serial No. 2022-507456, Final Notification of Reasons for Refusal mailed Jul. 4, 2023", with English translation, 10 pgs.

"Chinese Application Serial No. 202080064217.2, Office Action mailed Sep. 26, 2023", w/ English Translation, 25 pgs.

"Japanese Application Serial No. 2022-507456, Examiners Decision of Final Refusal mailed Nov. 28, 2023", w/ English Translation, 14 pgs.

"Japanese Application Serial No. 2022-507456, Response filed Oct. 10, 2023 to Final Notification of Reasons for Refusal mailed Jul. 4, 2023", w/ english claims, 19 pgs.

"Chinese Application Serial No. 202080064217.2, Response filed Jan. 30, 2024 to Office Action mailed Sep. 26, 2023", w english claims, 18 pgs.

* cited by examiner

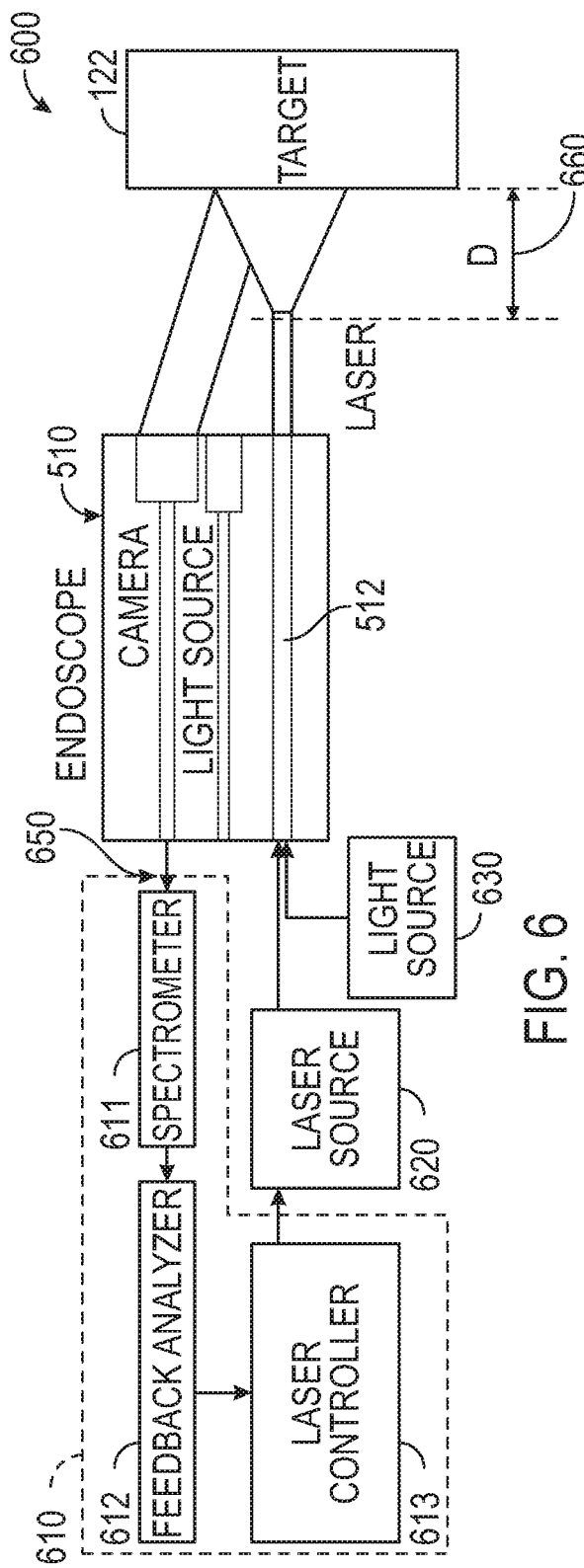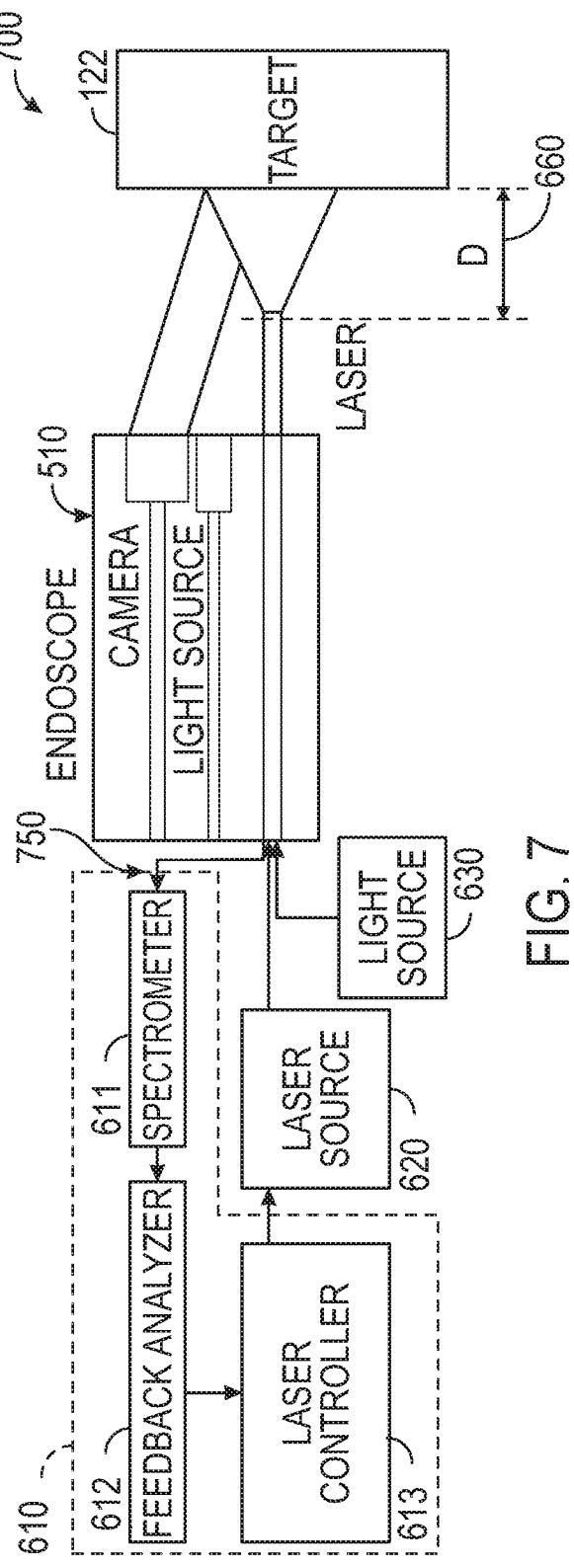

SELECTIVE LASER FIRING FOR TISSUE SAFETY

CLAIM OF PRIORITY

This application claims the benefit of priority under 35 U.S.C. § 119(e) of U.S. Provisional Patent Application Ser. No. 62/882,837, filed on Aug. 5, 2019, and U.S. Provisional Patent Application Ser. No. 63/017,450, filed on Apr. 29, 2020, which are herein incorporated by reference in their entireties.

TECHNICAL FIELD

This document relates generally to a laser surgical system, and more specifically relates to a laser endoscopy system for selectively applying surgical lasers to a target while maintaining tissue safety.

BACKGROUND

Endoscopes are typically used to provide access to an internal location of a patient so that a doctor is provided with visual access. Some endoscopes are used in minimally invasive surgery to remove unwanted tissue or foreign objects from the body of the patient. For example, a nephroscope is used by a clinician to inspect the renal system, and to perform various procedures under direct visual control. In a percutaneous nephrolithotomy (PCNL) procedure, a nephroscope is placed through the patient's flank into the renal pelvis. Calculi or mass from various regions of a body including, for example, urinary system, gallbladder, nasal passages, gastrointestinal tract, stomach, or tonsils, can be visualized and extracted.

Laser or plasma systems have been used for delivering surgical laser energy to various target treatment areas such as soft or hard tissue. Examples of the laser therapy include ablation, coagulation, vaporization, fragmentation, etc. In lithotripsy applications, laser has been used to break down calculi structures in kidney, gallbladder, ureter, among other stone-forming regions, or to ablate large calculi into smaller fragments. In endoscopic laser therapy, it is desirable that lasers be applied only to target treatment structures (e.g., calculi or cancerous tissue), and spare non-treatment tissue from unintended laser irradiation.

SUMMARY

The present document describes systems, devices, and methods for identifying different tissue or calculi types with distinct compositions in vivo during a medical procedure such as a laser endoscopy procedure, and automatically adjusting therapy in accordance with the identified tissue or calculus type. An exemplary electrosurgical treatment system comprises an electrosurgical energy system configured to generate electrosurgical energy for delivery to a target in a body of a subject, and a controller circuit configured to receive a signal reflected from the target in response to electromagnetic radiation produced by a light source, and generate one or more spectroscopic properties from the reflected signal. The controller circuit can identify the target as one of a plurality of structure types with respective distinct compositions using the one or more spectroscopic properties, and determine an operating mode of the electrosurgical energy system based on the identification of the target. In an example, the control circuit may control the electrosurgical energy system to deliver electrosurgical energy at a particular type of target of interest, such as a calculus type or cancerous tissue, and adjust laser setting based on the classified tissue type or calculus type.

Example 1 is an electrosurgical treatment system, comprising: an electrosurgical energy system configured to generate electrosurgical energy for delivery to a target in a body of a subject; and a controller circuit configured to: receive a signal reflected from the target in response to electromagnetic radiation produced by a light source; generate one or more spectroscopic properties from the received reflected signal; identify, using the one or more spectroscopic properties, the target as one of a plurality of structure types with respective distinct compositions; and determine an operating mode of the electrosurgical energy system based on the identification of the target, the operating mode including delivery or withhold delivery of the electrosurgical energy, or an energy parameter setting for the electrosurgical energy system.

In Example 2, the subject matter of Example 1 optionally includes, wherein the electrosurgical energy system includes a laser system configured to generate a laser beam for delivery to the target in the body of the subject, and the energy parameter setting includes a laser parameter setting.

In Example 3, the subject matter of Example 2 optionally includes, wherein the controller circuit is configured to: generate a reflectance spectrum using the received reflected signal, the reflectance spectrum representing reflectance intensities over a plurality of wavelengths; and generate one or more spectroscopic properties including extracting from the reflectance spectrum one or more spectral features including: a reflectance intensity at a specific wavelength; a statistical feature of reflectance over two or more different wavelengths; or a graphical feature of a graphical representation of the reflectance spectrum.

In Example 4, the subject matter of Example 3 optionally includes, wherein the controller circuit is configured to identify the target as one of a calculus structure or an anatomical structure using the one or more spectroscopic properties.

In Example 5, the subject matter of any one or more of Examples 3-4 optionally includes, wherein the controller circuit is configured to: classify the target as one of a plurality of calculi types with respective distinct compositions using the one or more spectroscopic properties; adjust a laser parameter setting for the laser system based on the classified calculus type of the target; and generate a control signal to the laser system to deliver a laser beam to the target of the classified calculus type in accordance with the adjusted laser parameter setting.

In Example 6, the subject matter of Example 5 optionally includes, wherein the controller circuit is configured to classify the target as one of renal calculi types including at least one of: a calcium phosphate (CaP) stone; a magnesium ammonium phosphate (MAP) stone; a monohydrate calcium oxalate (COM) stone; a cholesterol-based stone; a dihydrate calcium oxalate (COD) stone; or a uric acid (UA) stone.

In Example 7, the subject matter of any one or more of Examples 3-6 optionally includes, wherein the controller circuit is configured to: classify the target as one of a plurality of tissue types using the one or more spectroscopic properties; and determine an operating mode of the laser system based on the classified tissue type of the target.

In Example 8, the subject matter of Example 7 optionally includes, wherein the controller circuit is configured to: classify the target as a treatment area or a non-treatment area using the one or more spectroscopic properties; and generate a control signal to the laser system to deliver a laser beam to the treatment area, and to withhold delivery of a laser beam to the non-treatment area.

In Example 9, the subject matter of any one or more of Examples 7-8 optionally includes, wherein the controller circuit is configured to: classify the target as normal tissue or cancerous tissue using the one or more spectroscopic properties; and generate a control signal to the laser system to deliver a laser beam to the target of the classified cancerous tissue, and to withhold delivery of a laser beam if the target is classified as normal tissue.

In Example 10, the subject matter of any one or more of Examples 1-9 optionally includes, wherein the controller circuit is configured to determine the operating mode of the electrosurgical energy system including one of a first operating mode if the target is identified as a calculus structure, a second operating mode if the target is identified as an anatomical structure, or a third operating mode if the target is identified as neither an anatomical structure nor a calculus structure.

In Example 11, the subject matter of any one or more of Examples 2-9 optionally includes an endoscope coupled to the laser system, the endoscope including the controller circuit and at least one optical pathway configured to transmit one or more of the laser beam, the signal reflected from the target, or the electromagnetic radiation produced by the light source.

In Example 12, the subject matter of Example 11 optionally includes, wherein the controller circuit is further configured to: calculate a distance between the target and a distal end of the at least one optical pathway using at least one of the one or more spectroscopic properties; and determine an operating mode of the laser system including delivering the laser beam to the target if (1) the target is identified as a treatment structure type, and (2) the calculated distance is within a specified laser firing range.

In Example 13, the subject matter of any one or more of Examples 11-12 optionally includes, wherein the at least one optical pathway includes a first optical pathway configured to transmit the signal reflected from the target to a spectroscopic sensor coupled to the controller circuit.

In Example 14, the subject matter of Example 13 optionally includes, wherein the first optical pathway is further configured to transmit the laser beam to the target.

In Example 15, the subject matter of any one or more of Examples 13-14 optionally includes, wherein the first optical pathway is further configured to transmit the electromagnetic radiation from the light source to the target.

In Example 16, the subject matter of any one or more of Examples 13-15 optionally includes, wherein the at least one optical pathway includes a second optical pathway separate from the first optical pathway, the second optical pathway configured to transmit the laser beam to the target.

In Example 17, the subject matter of any one or more of Examples 11-16 optionally includes, wherein the controller circuit is configured to generate the one or more spectroscopic properties further using information about an outer diameter of the at least one optical pathway.

In Example 18, the subject matter of any one or more of Examples 11-17 optionally includes, wherein the controller circuit is configured to generate the one or more spectroscopic properties further using information about an angle of protrusion of a distal end of the at least one optical pathway relative to the endoscope.

In Example 19, the subject matter of any one or more of Examples 1-18 optionally includes, wherein the electromagnetic radiation produced by the light source includes one or more of: ultraviolet waves; visible light waves; or infrared waves.

In Example 20, the subject matter of any one or more of Examples 1-19 optionally includes, wherein the control circuit is coupled to a spectroscopic sensor configure to sense the signal reflected from the target in response to the electromagnetic radiation illuminating the target structure, the spectroscopic sensor including one or more of: a Fourier Transform Infrared (FTIR) spectrometer; a Raman spectrometer; a UV-VIS spectrometer; a UV-VIS-IR spectrometer; or a fluorescent spectrometer.

In Example 21, the subject matter of any one or more of Examples 1-20 optionally includes, wherein the control circuit is coupled to an imaging sensor configure to sense the signal reflected from the target in response to the electromagnetic radiation illuminating the target structure.

Example 22 is a method for controlling an electrosurgical energy system to deliver electrosurgical energy to a target in a body of a subject, the method comprising: illuminating the target with electromagnetic radiation produced by a light source; sensing, via a spectroscopic sensor coupled a controller circuit, a signal reflected from the target in response to the electromagnetic radiation; generating, via the controller circuit, one or more spectroscopic properties using the sensed reflected signal; identifying, via the controller circuit, the target as one of a plurality of structure types with respective distinct compositions using the one or more spectroscopic properties; and generating, via the controller circuit, a control signal to operate an electrosurgical energy system in an operating mode based on the identification of the target, the operating mode including delivery or withhold delivery of the electrosurgical energy, or an energy parameter setting for the electrosurgical energy system.

In Example 23, the subject matter of Example 22 optionally includes, wherein the control signal is generated to operate a laser system in an operating mode based on the identification of the target, the operating mode including delivery or withhold delivery of a laser beam, or a laser parameter setting for the laser system.

In Example 24, the subject matter of any one or more of Examples 22-23 optionally includes generating a reflectance spectrum using the sensed reflected signal, the reflectance spectrum representing reflectance intensities over a plurality of wavelengths, and wherein generating one or more spectroscopic properties includes extracting from the reflectance spectrum one or more spectral features including: a reflectance intensity at a specific wavelength; a statistical feature of reflectance over two or more different wavelengths; or a graphical feature of a graphical representation of the reflectance spectrum.

In Example 25, the subject matter of any one or more of Examples 23-24 optionally includes classifying the target as one of a plurality of calculi types with respective distinct compositions using the one or more spectroscopic properties, adjusting a laser parameter setting for the laser system based on the classified calculus type of the target, and generating a control signal to the laser system to deliver a laser beam to the target of the classified calculus type in accordance with the adjusted laser parameter setting.

In Example 26, the subject matter of any one or more of Examples 23-25 optionally includes classifying the target as one of a plurality of tissue types using the one or more spectroscopic properties, and determining an operating mode of the laser system based on the classified tissue type of the target.

In Example 27, the subject matter of Example 26 optionally includes: classifying the target as a treatment area or a non-treatment area using the one or more spectroscopic properties; and generating a control signal to the laser system to deliver a laser beam to the treatment area, and to withhold delivery of a laser beam to the non-treatment area.

In Example 28, the subject matter of any one or more of Examples 26-27 optionally include: classifying the target as normal tissue or cancerous tissue using the one or more spectroscopic properties; and generating a control signal to the laser system to deliver a laser beam to the target of the classified cancerous tissue, and to withhold delivery of a laser beam if the target is classified as normal tissue.

In Example 29, the subject matter of any one or more of Examples 23-28 optionally includes, wherein determining the operating mode of the electrosurgical energy system includes one of a first operating mode if the target is identified as a calculus structure, a second operating mode if the target is identified as an anatomical structure, or a third operating mode if the target is identified as neither an anatomical structure nor a calculus structure.

In Example 30, the subject matter of any one or more of Examples 23-29 optionally includes calculating a distance between the target and a distal end of an optical pathway associated with an endoscope using at least one of the one or more spectroscopic properties, and determine an operating mode of the laser system including delivering the laser beam to the target if (1) the target is identified as a treatment structure type, and (2) the calculated distance is within a specified laser filing range.

In Example 31, the subject matter of any one or more of Examples 23-30 optionally includes, wherein generating the one or more spectroscopic properties includes using geometry and positioning information about at least one optical pathway associated with an endoscope and configured to transmit one or more of the laser beam, the signal reflected from the target, or the electromagnetic radiation produced by the light source, wherein the geometry and positioning information includes at least one of an outer diameter of the at least one optical pathway, or an angle of protrusion of a distal end of the at least one optical pathway relative to the endoscope.

Example 32 is at least one non-transitory machine-readable storage medium that includes instructions that, when executed by one or more processors of a machine, cause the machine to perform operations comprising: illuminating a target in a body of a subject with electromagnetic radiation produced by a light source; receiving a signal reflected from the target in response to the electromagnetic radiation; generating one or more spectroscopic properties using the reflected signal; identifying, using the one or more spectroscopic properties, the target as one of a plurality of structure types with respective distinct compositions; and generating a control signal to operate an electrosurgical energy system in an operating mode based on the identification of the target, the operating mode including delivery or withhold delivery of electrosurgical energy, or an energy parameter setting for the electrosurgical energy system.

In Example 33, the subject matter of Example 32 optionally includes, wherein the control signal is generated to operate a laser system in an operating mode based on the identification of the target, the operating mode including delivery or withhold delivery of a laser beam, or a laser parameter setting for the laser system.

In Example 34, the subject matter of any one or more of Examples 32-33 optionally includes, wherein the instructions cause the machine to perform operations further comprising generating, using the received reflected signal, a reflectance spectrum representing reflectance intensities over a plurality of wavelengths, and wherein the operation of generating one or more spectroscopic properties includes extracting from the reflectance spectrum one or more spectral features including: a reflectance intensity at a specific wavelength; a statistical feature of reflectance over two or more different wavelengths; or a graphical feature of a graphical representation of the reflectance spectrum.

In Example 35, the subject matter of any one or more of Examples 32-34 optionally includes, wherein the operation of identifying the target as one of a plurality of structure types includes identifying the target as one of a calculus structure or an anatomical structure using the one or more spectroscopic properties.

In Example 36, the subject matter of any one or more of Examples 32-35 optionally includes, wherein the instructions cause the machine to perform operations further comprising: classifying the target as one of a plurality of calculi types with respective distinct compositions using the one or more spectroscopic properties; adjusting a laser parameter setting for the electrosurgical energy system based on the classified calculus type of the target; and generating a control signal to the electrosurgical energy system to deliver a laser beam to the target of the classified calculus type in accordance with the adjusted laser parameter setting.

In Example 37, the subject matter of any one or more of Examples 32-36 optionally includes, wherein the instructions cause the machine to perform operations further comprising: classifying the target as one of a plurality of tissue types using the one or more spectroscopic properties; and determining an operating mode of the laser system based on the classified tissue type of the target.

In Example 38, the subject matter of any one or more of Examples 32-37 optionally includes, wherein the instructions cause the machine to perform operations further comprising: calculating a distance between the target and a distal end of an optical pathway associated with an endoscope using at least one of the one or more spectroscopic properties; and determine an operating mode of the laser system including delivering the laser beam to the target if (1) the target is identified as a treatment structure type, and (2) the calculated distance is within a specified laser firing range.

In Example 39, the subject matter of any one or more of Examples 32-38 optionally includes, wherein the operation of generating the one or more spectroscopic properties includes using geometry and positioning information about at least one optical pathway associated with an endoscope and configured to transmit one or more of the laser beam, the signal reflected from the target, or the electromagnetic radiation produced by the light source, wherein the geometry and positioning information includes at least one of an outer diameter of the at least one optical pathway, or an angle of protrusion of a distal end of the at least one optical pathway relative to the endoscope.

This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense.

The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 6 illustrates an example of a laser treatment system including an endoscope integrated with a feedback-controlled laser treatment system receiving a camera feedback.

FIG. 7 illustrates an example of a laser treatment system including an endoscope integrated with the feedback-controlled laser treatment system receiving a spectroscopic sensor feedback.

DETAILED DESCRIPTION

Figure 1:
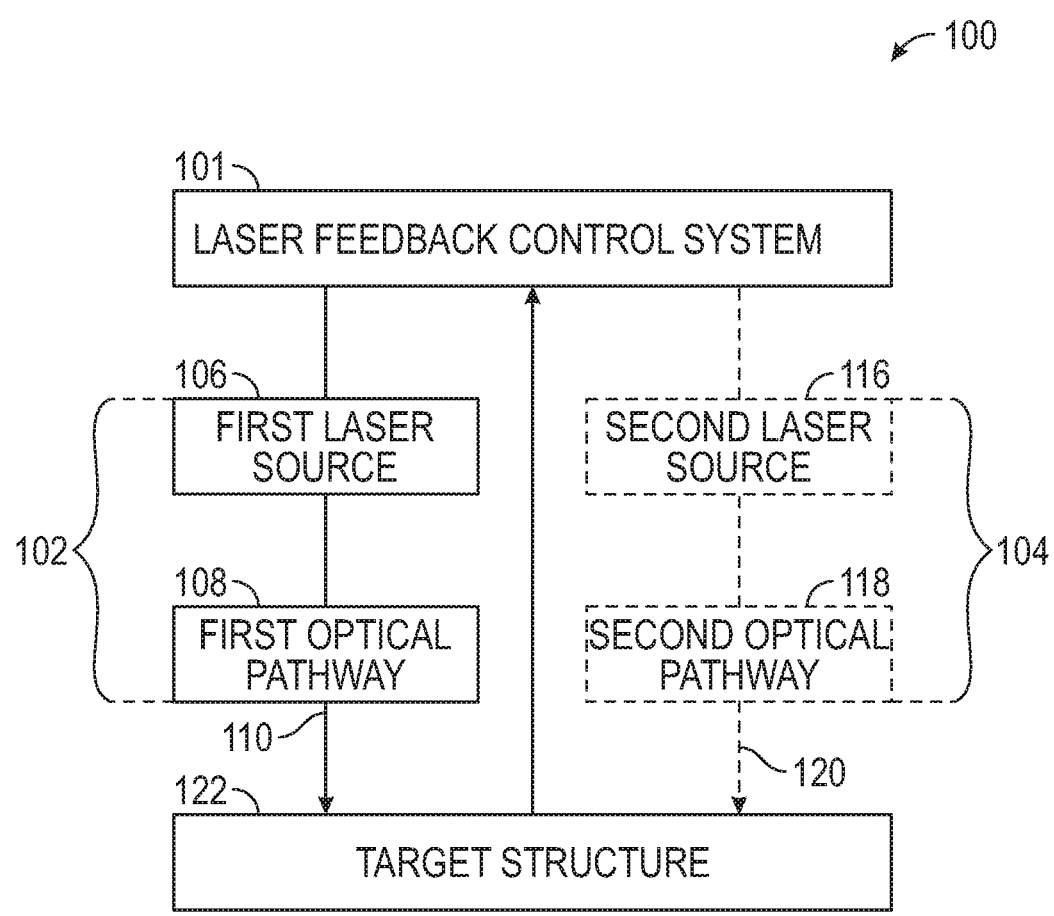
FIG. 1 is a block diagram illustrating an example of a laser treatment system configured to provide laser therapy to a target structure in a body, such as an anatomical structure or a calculus structure.

Laser endoscopy is a medical procedure of viewing and operating on an internal organ, and delivering surgical laser to a target body region to achieve a particular diagnostic or therapeutic effect. Laser endoscopy have been used for treatment of soft and hard tissue (e.g., damaging or destroying cancer cells), or in lithotripsy applications. For example, in PCNL, a practitioner can insert a rigid scope through an incision in a patient's back and into the patient's kidney. Through the scope, the practitioner can locate certain stones in the kidney or upper ureter, break the stones into smaller fragments by illuminating the stone, through the scope, with relatively high-powered infrared laser beam. The laser beam can ablate a stone into smaller fragments. The stone fragments can then be withdrawn from the kidney. The scope can include an endoscope, a nephroscope, and/or a cystoscope.

In endoscopic laser therapy, it is desirable to recognize different tissue, apply laser energy only to target treatment structures (e.g., cancerous tissue, or a particular calculus type), and avoid or reduce exposing non-treatment tissue (e.g., normal tissue) to laser irradiation. Conventionally, the recognition of a target treatment structure of interest is performed manually by an operator, such as by visualizing the target surgical site and its surrounding environment through an endoscope. Such a manual approach can lack accuracy at least in some cases, such as due to a tight access to an operation site that offers a limited surgical view, and may not determine composition of the target. Biopsy techniques have been used to extract the target structure (e.g., tissue) out of the body to analyze its composition in vitro. However, in many clinical applications, it is desirable to determine tissue composition in vivo to reduce surgery time and complexity and improve therapy efficacy. For example, in laser lithotripsy that applies laser to break apart or dust calculi, automatic and in vivo recognition of calculi of a particular type (e.g., chemical composition of a kidney or pancreobiliary or gallbladder stone) and distinguishing it from surrounding tissue would allow a physician to adjust a laser setting (e.g., power, exposure time, or firing angle) to more effectively ablate the target stone, while at the same time avoiding irradiating non-treatment tissue neighboring the target stone.

Conventional endoscopic laser therapy also has a limitation that tissue type (e.g., composition) cannot be continuously monitored in a procedure. There are many moving parts during an endoscopic procedure, and the tissue viewed at from the endoscope may change throughout the procedure. Because the conventional biopsy techniques require the removal of a tissue sample to identify the composition, they cannot monitor the composition of the tissue throughout the procedure. Continuous monitoring and recognition of structure type (e.g., soft or hard tissue type, normal tissue versus cancerous tissue, or composition of calculi structures) at the tip of the endoscope may give physicians more information to better adapt the treatment during the procedure. For example, if a physician is dusting a renal calculi that has a hard surface, but a soft core, continuous tissue composition information through the endoscope can allow the physician to adjust the laser setting based on the continuously detected stone surface composition, such as from a first setting that perform better on the hard surface of the stone to a second different setting that perform better on the soft core of the stone.

For at least the above reasons, the present inventors have recognized an unmet need for systems and methods that are capable of identifying different structure types with respective distinct compositions in vivo, and adjusting therapy according to the identification of structure types.

Described herein are systems, devices, and methods for identifying different structure types with distinct composition in vivo and adjusting surgical laser output accordingly in a medical procedure. An exemplary laser treatment system comprises a laser system configured to generate a laser beam for delivery to a target in a body, and a controller circuit configured to receive a signal reflected from the target in response to electromagnetic radiation produced by a light source, and generate one or more spectroscopic properties from the reflected signal. The controller circuit can identify the target as one of a plurality of structure types, such as tissue types or calculi types with distinct compositions, using the one or more spectroscopic properties. The laser system can be controlled to operate in an operating mode based on the target identification. The operating mode may include delivery or withhold delivery of the laser beam, or a laser parameter setting for the laser system. In an example, the control circuit may control the laser system to fire a laser beam at a target of interest, such as a calculus type or cancerous tissue, and adjust laser setting based on the classified tissue type or calculus type.

The systems, devices, and methods according to various embodiments discussed herein provide improved in vivo target structure diagnostics and laser therapy. Features described herein may be used in regard to an endoscope, laser surgery, laser lithotripsy, laser settings, and/or spectroscopy, Examples of targets and applications may include laser lithotripsy of renal calculi and laser incision or vaporization of soft tissue. In an example of endoscopic system that incorporate the features as described herein, tissue or calculi types or composition may be identified and monitored in vivo. Automatic and in vivo identification of tissue types or calculi types such as chemical composition of a target many be used to adjust laser settings for optimum delivery of laser energy. The capability of continuous monitoring and identification of tissue types or calculi types allow for the instant adjustment of laser settings. For example, according to various aspects of the present document, a laser system may provide input data to another system such as an image processor whereby the procedure monitor may display information to the user relevant to the medical procedure. One example of this is to more clearly identify different soft tissues in the field of view during a procedure, vasculature, capsular tissue, and different chemical compositions in the same target, such as a stone for example. With improved recognition and classification of target structure, the patient can be protected from accidental laser firing or misplaced laser firing, and improved therapy efficacy and tissue safety can be achieved.

In accordance to various embodiments discussed herein, the present document also provides techniques for estimating and controlling a distance between a laser fiber and a target structure. For example, if an appropriate targeted element (e.g., cancerous lesion or calculi) is not within the range of the laser, the laser may be "locked", i.e., prevented from firing. For example, when the present technology is used in a laser lithotripsy procedure, the laser may be locked if no stone is within laser range (e.g., only tissue is within laser range), This locking control can also be used to ensure a target is within optimum firing distance to improve performance of an existing laser lithotripsy system, conserve power, enhance patient safety, and improves efficacy of stone ablation.

FIG. 1 is a block diagram illustrating an example of a laser treatment system 100 configured to provide laser treatment to a target structure 122 in a body of a subject, such as anatomical structure (e.g., soft tissue, hard tissue, or abnormal such as cancerous tissue) or calculus structure (e.g., kidney or pancreobiliary or gallbladder stone). The laser treatment system 100 may include a laser feedback control system 101 and at least one laser system 102. The laser feedback control system 101 may be configured to receive a signal reflected from the target in response to electromagnetic radiation produced by a light source, generate one or more spectroscopic properties using the reflected signal from the target, identify the target as one of a plurality of structure types with respective distinct compositions (e.g., a calculus type or an tissue type), and determine an operating mode of the laser system based on the identified structure type. The laser feedback control system 101 may be used in various applications, such as industrial and/or medical applications for treatment of soft (e.g., non-calcified) or hard (e.g., calcified) tissue, or calculi structures such as kidney or pancreobiliary or gallbladder stones. In some examples, the laser treatment system 100 may deliver precisely controlled therapeutic treatment of tissue or other anatomical structures (e.g., tissue ablation, coagulation, vaporization, or the like) or treatment of non-anatomical structures (e.g., ablation or dusting of calculi structures).

The laser feedback control system 101 may be in operative communication with one or more laser systems. FIG. 1 shows the laser feedback system connected to a first laser system 102 and optionally (shown in dotted lines) to a second laser system 104. Additional laser systems are contemplated within the scope of the present disclosure. The first laser system 102 may include a first laser source 106, and associated components such as power supply, display, cooling systems and the like. The first laser system 102 may also include a first optical pathway 108 operatively coupled with the first laser source 106. In an example, the first optical pathway 108 includes an optical fiber. The first optical pathway 108 may be configured to transmit laser beams from the first laser source 106 to the target structure 122.

The laser feedback control system 101 may analyze feedback signals 130 from the target structure 122, and control the first laser system 102 and/or the second laser system 104 to generate suitable laser outputs for providing a desired therapeutic effect. For instance, the laser feedback control system 101 may monitor properties of the target structure 122 during a therapeutic procedure (e.g., ablating calculi such as kidney stones into smaller fragments) to determine if the tissue was suitably ablated prior to another therapeutic procedure (e.g., coagulation of blood vessels).

In an example, the first laser source 106 may be configured to provide a first output 110. The first output 110 may extend over a first wavelength range, such as one that corresponds to a portion of the absorption spectrum of the target structure 122, The first output 110 may provide effective ablation and/or carbonation of the target structure 122 since the first output 110 is over a wavelength range that corresponds to the absorption spectrum of the tissue.

In an example, the first laser source 106 may be configured such that the first output 110 emitted at the first wavelength range corresponds to high absorption (e.g., exceeding about 250 cm$^{-1}$) of the incident first output 110 by the tissue. In example aspects, the first laser source 106 may emit first output 110 between about 1900 nanometers (nm) and about 3000 nm (e.g., corresponding to high absorption by water) and/or between about 400 nm and about 520 nm (e.g., corresponding to high absorption by oxy-hemoglobin and/or deoxy-hemoglobin). Appreciably, there are two main mechanisms of light interaction with a tissue: absorption and scattering. When the absorption of a tissue is high (absorption coefficient exceeding 250 cm$^{-1}$) the first absorption mechanism dominates, and when the absorption is low (absorption coefficient less than 250 cm$^{-}$), for example lasers at 800-1100 nm wavelength range, the scattering mechanism dominates.

Various commercially available medical-grade laser systems may be suitable for the first laser source 106. For instance, semiconductor lasers such as InXGaI-XN semiconductor lasers providing the first output 110 in the first wavelength range of about 515 nm and about 520 nm or between about 370 nm and about 493 nm may be used. Alternatively, infrared (IR) lasers such as those summarized in Table 1 below may be used.

TABLE 1

Example List of suitable IR lasers

| Laser | Wavelength λ (nm) | Absorption Coefficient $\mu_s$ (cm$^{-1}$) | Optical Penetration Depth δ (μm) |
|---|---|---|---|
| Thulium fiber laser: | 1908 | 88/150 | 114/67 |
| Thulium fiber laser: | 1940 | 120/135 | 83/75 |
| Thulium: YAG: | 2010 | 62/60 | 161/167 |
| Holmium: YAG: | 2120 | 24/24 | 417/417 |
| Erbium: YAG: | 2940 | 12,000/1.000 | 1/10 |

The optional second laser system 104 may include a second laser source 116 for providing a second output 120, and associated components, such as power supply, display, cooling systems and the like. The second laser system 104 may either be operatively separated from or, in the alternative, operatively coupled to the first laser source 106. In some embodiments, the second laser system 104 may include a second optical fiber 118 (separate from the first optical pathway 108) operatively coupled to the second laser source 116 for transmitting the second output 120. Alternatively, the first optical pathway 108 may be configured to transmit both the first output 110 and the second output 120.

In certain aspects, the second output 120 may extend over a second wavelength range, distinct from the first wavelength range. Accordingly, there may not be any overlap between the first wavelength range and the second wavelength range. Alternatively, the first wavelength range and the second wavelength range may have at least a partial overlap with each other. In advantageous aspects of the present disclosure, the second wavelength range may not correspond to portions of the absorption spectrum of the target structure 122 where incident radiation is strongly absorbed by tissue that has not been previously ablated or carbonized. In some such aspects, the second output 120 may advantageously not ablate uncarbonized tissue. Further, in another embodiment, the second output 120 may ablate carbonized tissue that has been previously ablated. In additional embodiments, the second output 120 may provide additional therapeutic effects. For instance, the second output 120 may be more suitable for coagulating tissue or blood vessels.

Figure 2:
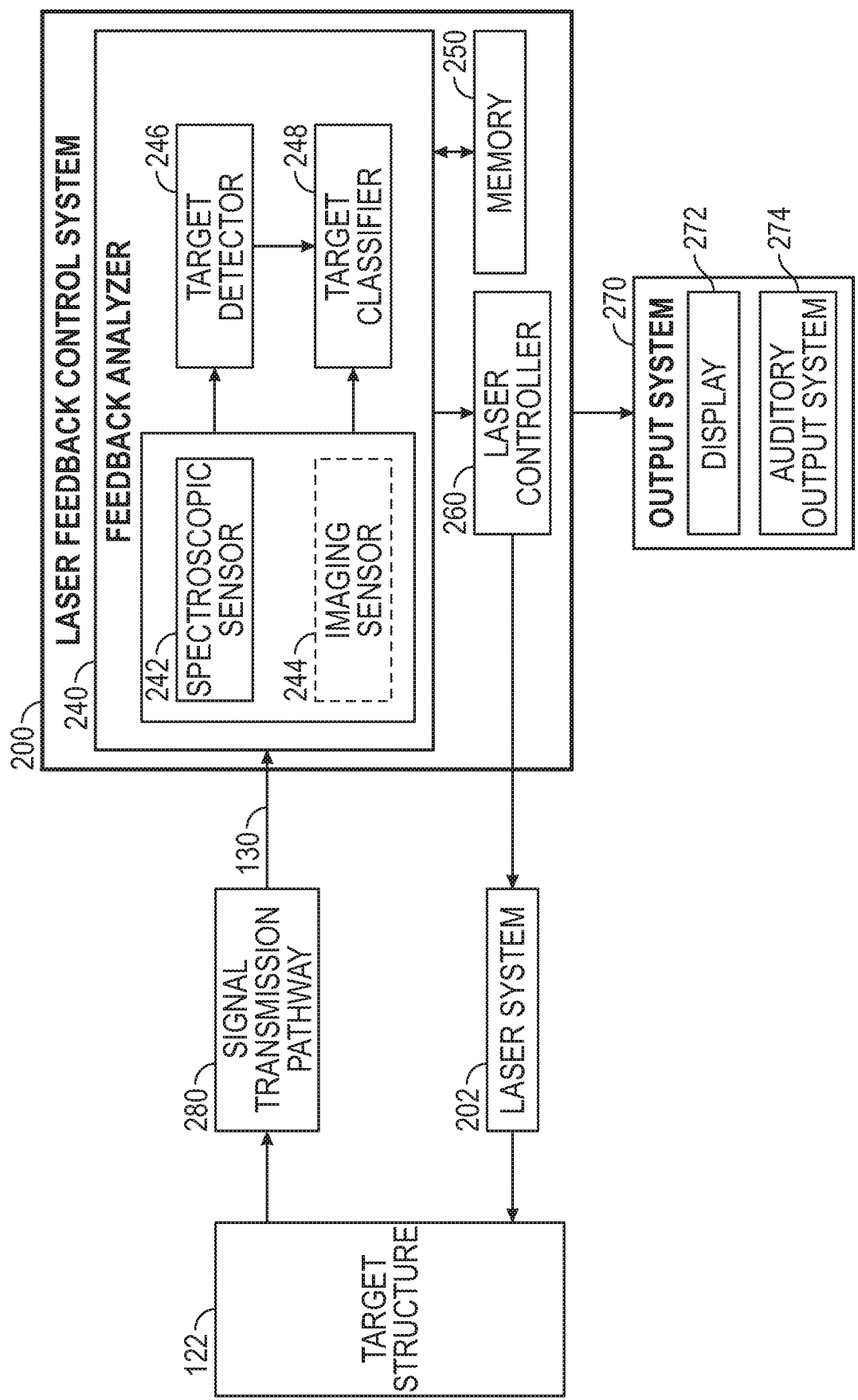
FIG. 2 is a block diagram illustrating a laser feedback control system and a part of the environment in which said system may be used.

FIG. 2 is a block diagram illustrating a laser feedback control system 200 and at least a part of the environment in which it may be used. The laser feedback control system 200, which is an example of the laser feedback control system 101, may include a feedback analyzer 240, a memory 250, and a laser controller 260. The feedback analyzer 240 may, according to one aspect of the subject matter described herein, include a spectroscopic sensor 242 configured to sense spectroscopic signal reflected from the target structure 122, and generate one or more spectroscopic properties from the reflected signal. The spectroscopic properties may include characteristics such as reflectivity, reflectance spectrum, absorption index, and the like. Examples of the spectroscopic sensor 242 may include a Fourier Transform Infrared (FTIR) spectrometer, a Raman spectrometer, a UV-VIS spectrometer, a UV-VIS-IR spectrometer, or a fluorescent spectrometer, among others. Each spectroscopic sensor 242 corresponds to a spectroscopy technique. For example, UV-VIS reflection spectroscopy may be used to gather information from the light reflected off an object similar to the information yielded from the eye or a color image made by a high resolution camera, but more quantitatively and objectively. The reflection spectroscopy may offer information about the material since light reflection and absorption depends on its chemical composition and surface properties, information about both surface and bulk properties of the sample may be obtained using this technique. The reflection spectroscopy may be used to recognize composition of hard or soft tissue, Fluorescent spectroscopy is a type of electromagnetic spectroscopy that analyzes fluorescence from a sample. It involves using a beam of light, usually ultraviolet, that excites a material compound and causes the material compound to emit light, typically in visible or IR area. The method may be applied for analysis of some organic components such as hard and soft tissue. FTIR spectroscopy may be used for rapid materials analysis, and has relatively good spatial resolution and gives information about the chemical composition of the material. Raman spectroscopy may be used for identifying hard and soft tissue components. As a high spatial resolution technique, it is also useful for determining distribution of components within a target.

The spectroscopy techniques as described above may be used alone or in combination to analyze the feedback signals 130 reflected from the target structure 122 to create the spectroscopic feedback, and to extract spectroscopic properties indicative of structure types with respective distinct compositions.

The feedback analyzer 240 may optionally include an imaging sensor 244. Examples of the imaging sensor 244 may include an imaging camera, such as a CCD or CMOS camera sensitive in ultraviolet (UV), visible (VIS) or infrared (IR) wavelengths in an embodiment. In some embodiments, the spectroscopic sensor 242 may include more than a single type of spectrometer or imaging camera listed herein to enhance sensing and detection of various features (e.g., carbonized and non-carbonized tissue, vasculature, and the like).

In some examples, the spectroscopic sensor 242 may include any of the spectrometers listed herein, and may additionally rely on imaging capabilities of an endoscope used during a therapeutic procedure. For instance, an endoscope may be used for visualizing an anatomical feature during a therapeutic procedure (e.g., laser ablation of a tumor). In such cases, the imaging capabilities of the endoscope may be augmented by the spectroscopic sensor 242. For example, conventional endoscopes may provide narrow band imaging suitable for enhanced visualization of anatomical features (e.g., lesions, tumors, vasculature, and the like). Combining the spectroscopic sensor 242 with the endoscopic imaging (white light and/or narrow band imaging) may increase detection of tissue properties, such as level of carbonization, to precisely control the delivery of therapeutic treatment.

In an example, the spectroscopic sensor 242 may be operatively coupled to a signal transmission pathway 280. The signal transmission pathway 280 may include optical fiber with optical properties suitable for transmission of spectroscopic signals reflected from the tissue to the spectroscopic sensor 242. Alternatively, the spectroscopic sensor 242 may be operatively coupled to the first optical pathway 108 of the first laser system 102 and/or the second optical pathway 118 of the second laser system 104 and thereby detect spectroscopic signals via the first optical pathway 108 and/or the second optical pathway 118.

The feedback analyzer 240 may include one or more of a target detector 246 or a target classifier 248. The target detector 246 may be configured to identify the target structure 122 as one of a plurality of structure categories using the spectroscopic properties such as generated by the spectroscopic sensor 242, optionally in combination with the imaging properties sensed by the optional imaging sensor 244. In an example, the target detector 246 may identify the target structure 122 as a category of calculus structure or as a category of anatomical structure using one or more spectroscopic properties. Examples of calculus structure may include stones or stone fragments in various stone-forming regions such as urinary system, gallbladder, nasal passages, gastrointestinal tract, stomach, or tonsils. Examples of the anatomical structure may include soft tissue (e.g., muscles, tendons, ligaments, blood vessels, fascia, skin, fat, and fibrous tissues), hard tissue such as bone, connective tissue such as cartilage, among others.

In an example, the feedback analyzer 240 may generate a reflectance spectrum using the received reflected signal, and extract one or more spectral features from the reflectance spectrum. The reflectance spectrum represents reflectance intensities over a plurality of wavelengths. Reflectance can be determined as a fraction of incident electromagnetic power reflected at a material interface. It represents the effectiveness of the material surface in reflecting radiant energy, such as electromagnetic radiation emitted from a light source. The reflectance spectrum may be formatted as a data array or a graphical representation also referred to a spectral reflectance curve. In an example, the reflectance spectrum represents reflectance over wavelengths in a range of approximately 400-1000 nm.

Figure 3A:
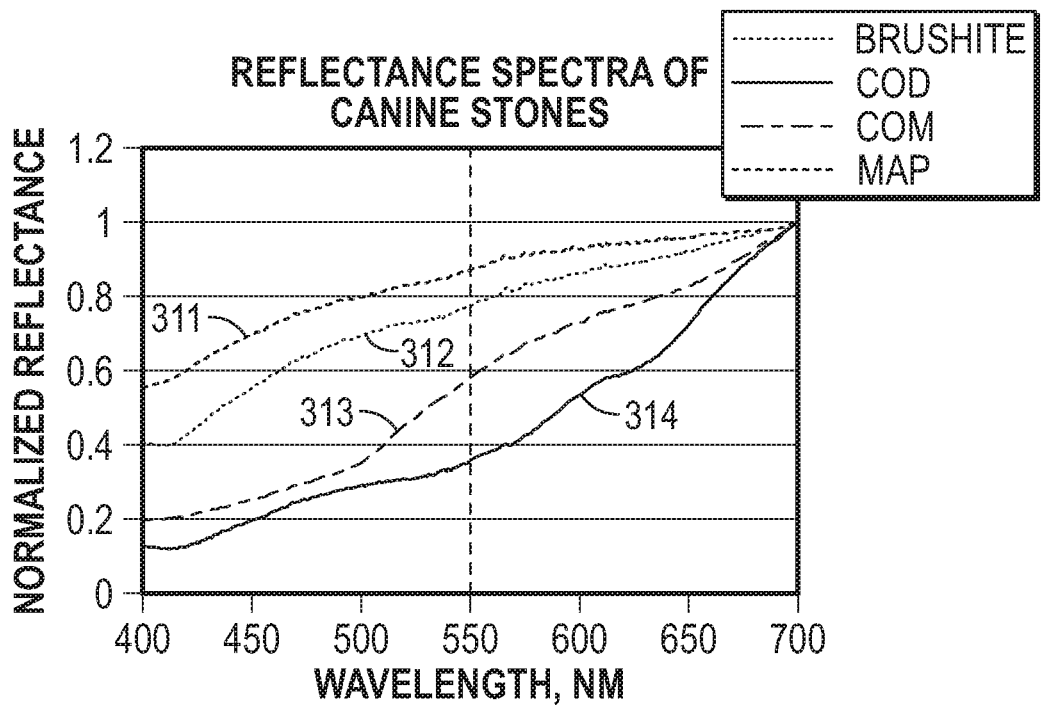
FIG. 3A is a diagram illustrating examples of normalized reflectance spectra of different kidney stone types.
Figure 3B:
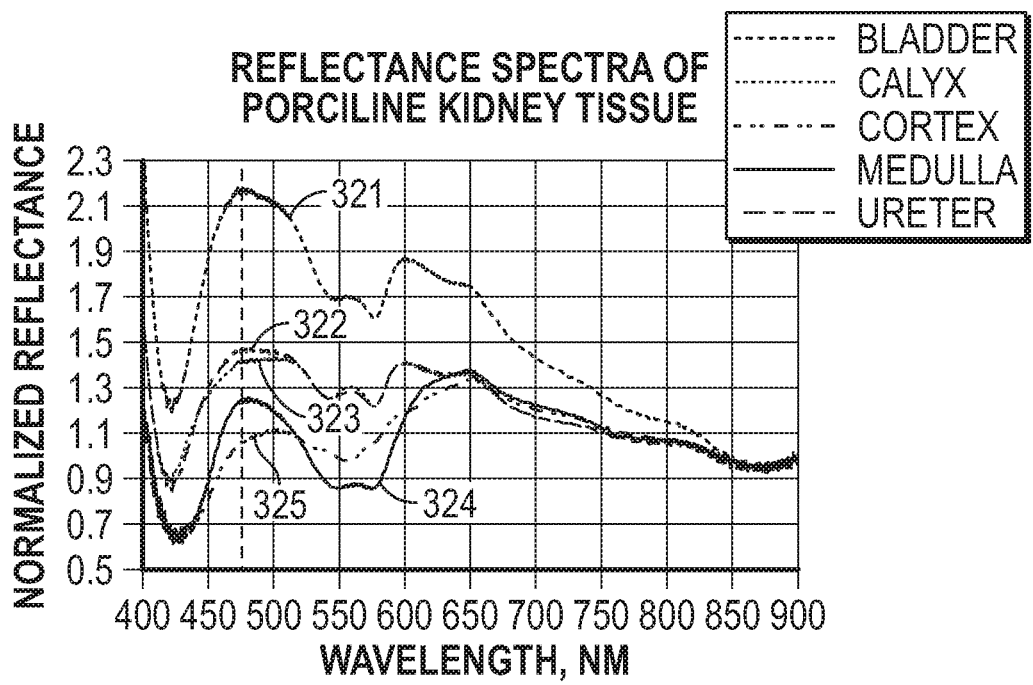
FIG. 3B is a diagram illustrates examples of normalized reflectance spectra of different kidney tissue types.

Referring to FIGS. 3A-3B, different categories of structures may have different reflectance intensities. For example, reflectance spectrum of a calculus structure (e.g., a kidney stone) may be different from a reflectance spectrum of an anatomical structure (e.g., soft or hard tissue of a subject). By way of example, FIG. 3A illustrates examples of normalized reflectance spectra of different kidney stone types. The reflectance spectra correspond to a wavelength range of approximately 400-700 nm, and are normalized with respect to the reflectance intensity at 700 nm. By way of example, FIG. 3B illustrates normalized reflectance spectra of different kidney tissue types. The reflectance spectra correspond to a wavelength range of approximately 400-900 nm, and are normalized with respect to the reflectance intensity at 900 nm.

As illustrated in FIG. 3A, the reflectance spectra of kidney stones demonstrate near monotonic increase in reflectance as the wavelength increase from 400-700 nm. In contrast, as illustrated in FIG. 3B, the reflectance spectra of kidney tissue demonstrate significant variation in reflectance in the wavelength range 400-650 nm, and near monotonic decrease in reflectance as the wavelength increases from 650 nm to 850 nm.

One or more spectral features may be extracted from a reflectance spectrum or normalized reflectance spectrum of a known calculus structure, as illustrated in FIG. 3A (hereinafter referred to as "calculi reflectance features"). Similarly, one or more spectral features may be extracted from a reflectance spectrum or normalized reflectance spectrum of a known anatomical structure such as shown in FIG. 3B (hereinafter referred to as "tissue reflectance features"). Examples of the characteristic reflectance features may include reflectance spectrum (or normalized reflectance spectrum) at a specific wavelength or over a wavelength range, a statistical value calculated from the reflectance spectrum (e.g., a variation of reflectance over two or more different wavelengths, a rate of change of reflectance over a range of wavelengths, or the like), or a graphical feature representing the morphology of at least a portion of the spectral reflectance curve (e.g., a slope, a curvature, a segment of the curve, or the like). The calculi reflectance features and the tissue reflectance features may be stored in the memory 250 of the laser feedback control system 200.

To identify the target structure 122 as either a calculus structure or an anatomical structure, in one example, the target detector 246 may extract one or more target reflectance features from a reflectance spectrum generated from the spectroscopic signal reflected from the target structure 122. The target detector 246 may identify the target structure 122 as a calculus structure if the target reflectance feature exceeds a feature threshold or falls within a value range, or as kidney tissue if the target reflectance feature falls below the feature threshold or falls outside the value range. Said feature threshold or value range may be determined using the calculi reflectance features and the tissue reflectance features. In an example, the feature threshold may be determined as one that separates the calculi reflectance features and the tissue reflectance features with a specified margin.

In some examples, the target detector 246 may trend the reflectance intensities of the target structure 122 over a range of wavelengths, and identify the target structure 122 based on the trend of the reflectance intensities (or the "reflectance trend"). In an example, the reflectance trend may be generated within a first range of 400-550 nm. The target structure 122 may be identified as a calculus structure if a monotonic increase reflectance trend is present in the first wavelength range demonstrate. The target structure 122 may be identified as kidney tissue if no monotonic increase reflectance trend is present in the first wavelength range. In another example, the reflectance trend may be generated within a second range of 650-700 nm. The target structure 122 may be identified as a calculus structure if a monotonic increase reflectance trend is present in the second wavelength range. The target structure 122 may be identified as kidney tissue if a monotonic decrease trend is present in the second wavelength range.

In another example, the target detector 246 may identify the target structure 122 as a calculus structure or an anatomical structure using a template matching approach. The target reflectance feature may be compared to at least one of the calculi reflectance features or at least one of the tissue reflectance features stored in the memory 250 to determine if a matching criterion is satisfied. For example, the target structure 122 may be identified as a calculus structure if a dissimilarity metric between the target reflectance feature and the calculi reflectance feature is below a first similarity threshold, or identified as kidney tissue if a dissimilarity metric between the target reflectance feature and the tissue reflectance feature is below a second similarity threshold.

In addition to the inter-category difference in reflectance spectra such as between a calculus structure and an anatomical structure as illustrated and contrasted between FIGS. 3A and 3B, different structure types within the same category may demonstrate different reflectance properties such as reflectance spectra. By way of example, FIG. 3A illustrates an example of intra-category difference in reflectance spectra among a plurality of calculi types. As illustrated therein, across a wavelength range of 400-700 nm, brushite stone (which is a type of calcium phosphate (CaP) stone) 311 has higher normalized reflectance than dihydrate calcium oxalate (COD) stone 312, which has higher normalized reflectance than monohydrate calcium oxalate (COM) stone 313, which has higher normalized reflectance than magnesium ammonium phosphate (MAP) stone 314. By way of example, FIG. 3B illustrates an intra-category difference in reflectance spectra among a plurality of kidney tissue types. As illustrated therein, the normalized reflectance of bladder 321 tends to be higher than the normalized reflectance of ureter 322, calyx 323, medulla 324, and cortex 325, across a wavelength range of 400-900 nm. Within certain wavelength range (e.g., 450-500 nm), ureter 322 has a higher normalized reflectance than calyx 323, which has higher normalized reflectance than medulla 324, which has higher normalized reflectance than cortex 325.

The target classifier 248 may use intra-category difference in reflectance spectra among different structure types of the same category as described above to classify the target structure 122 as one of a plurality of structure types of the same category, such as a particular tissue type within an identified category of anatomical structure, or as a particular calculus type within an identified category of calculus structure. In an example, the target classifier 248 may classify an identified renal calculus as one of stone types with distinct chemical compositions, such as one of a CaP stone, a MAP stone, a COM stone, a COD stone, a cholesterol-based stone, or a uric acid (UA) stone. The classification may be based on one or more of reflectance at a specific wavelength, a statistical feature (e.g., variance or other variation metric) of reflectance over two or more different wavelengths, or a graphical feature generated from a graphical representation of the reflectance spectrum. For example, based on the distinct normalized reflectance spectra among various stone types as shown in FIG. 3A, the target classifier 248 may compare a normalized reflectance at a specific wavelength (e.g., 550 nm) or wavelength range to one or more thresholds to classify the target structure 122 as a particular stone type.

In another example, the target classifier 248 may be configured to classify an identified anatomical structure as one of plurality of tissue types using the one or more spectroscopic properties. In an example, the target classifier 248 may be configured to classify the identified renal tissue as one of tissue types with distinct anatomical locations, such as calyx tissue, cortex tissue, medulla tissue, or ureter tissue. For example, based on the distinct normalized reflectance spectra among various tissue types as shown in FIG. 3B, the target classifier 248 may classify the target structure 122 as a particular tissue type based on a comparison between the normalized reflectance at a specific wavelength (e.g., 480 nm) or wavelength range and one or more reflectance thresholds.

In another example, the target classifier 248 may be configured to classify an identified anatomical structure as normal tissue or abnormal tissue (e.g., cancerous tissue). Normal and cancerous tissue may demonstrate distinct reflectance spectra with different shapes, peak locations (i.e., the wavelength at which the reflectance spectrum reaches a peak value across a wavelength range). The classifier 248 may be configured to classify an identified anatomical structure as a treatment area (e.g., tumor or polyp intended for removal) or a non-treatment area (e.g., blood vessels, muscle, etc.). The classification may be based on one or more of reflectance at a specific wavelength, a statistical feature (e.g., variance or other variation metric) of reflectance over two or more different wavelengths, or a graphical feature (e.g., a slope) generated from a graphical representation of the reflectance spectrum.

Referring back to FIG. 2, the laser controller 260 may be in operative communication with the feedback analyzer 240 and a laser system 202. The laser system 202 may represent the first laser system 102, the optional second laser system 104, and/or any additional laser systems. The laser controller 260 may control the laser system 202 operatively connected thereto according to one or more control algorithms described herein to control the laser outputs from the one or more laser systems to produce a desired therapeutic effect in the target structure 122.

According to example embodiments, the laser controller 260 may include processors, such as microprocessors, digital signal processors (DSPs), application specific integrated circuits (ASICs), field programmable gate arrays (FPGAs), or any other equivalent integrated or discrete logic circuitry, as well as any combinations of such components for performing one or more of the functions attributed to the laser controller 260. Optionally, the laser controller 260 may be coupled by wired or wireless connections to the feedback analyzer 240 and the laser system 202. The laser controller 260 may communicate with the feedback analyzer 240 (e.g., over wired or wireless connections), and determine an operating mode of the laser system 202 based on the identification of the target structure 122 (such as determined by the target detector 246), or based on the classification of the target structure 122 (such as determined by the target classifier 248).

In some examples, the laser system 202 may be associated with one of two distinct operating modes or states: a first state wherein the laser system 202 generates a laser output, and a second state where a laser system 202 does not generate a laser output. For instance, the first laser system 102 may have a first state where a first output 110 (e.g., over the first wavelength range) is generated, and a second state where the first output 110 is not generated. Similarly, the second laser system 104 may have a first state where a second output 120 (e.g., over the second wavelength range) is generated, and a second state where the second output 120 is not generated. In such embodiments, the laser controller 260 may control the laser system 220 by sending control signals that change the operating state the laser system from the first state to the second state, or from the second state to the first state. In some examples, the laser system 202 may have additional states, for instance, a third state where a laser output in accordance with a different laser irradiation parameter setting (e.g., different wavelength range, and/or power output) is generated. Accordingly, additional control signals may be sent by the laser controller 260 to the laser system(s) to change their states from their current state to one or more additional states (e.g., first state to third state, second state to third state, third state to first state, and third state to second state) to generate laser outputs that provide a desired therapeutic effect.

In an example, the laser controller 260 may generate a first control signal to the laser system 202 to operate on a first operating mode if the target is identified as a calculus structure, generate a second control signal to the laser system to operate on a second operating mode if the target is identified as an anatomical structure, and generate a third control signal to the laser system to operate on a third operating mode if the target is identified as neither an anatomical structure nor a calculus structure. In an example, the first operating mode may include activating the laser system 202 to deliver a laser beam programmed with a first irradiation parameter setting to ablate or dust the identified calculi, such as kidney stones. In an example, the second operating mode may include withholding laser delivery, or delivering a laser beam programmed with a second irradiation parameter setting different from the first irradiation parameter setting to an identified tissue. In an example, the third operating mode may include deactivating the laser system 202 from delivery of laser energy. The laser irradiation parameters may include wavelength, power, power density, pulse parameters (e.g., pulse width, pulse rate, amplitude, duty cycle), exposure time, total dose or energy, among others.

In some examples, the laser controller 260 may determine the operating mode of the laser system 202 based on the classification of the target structure 122 as one of a plurality of calculi types, such as CaP stone, a MAP stone, a COM stone, a COD stone, a cholesterol-based stone, or a uric acid (UA) stone, as determined by the target classifier 248. The laser controller 260 may adjust the irradiation parameter setting based on the classification of calculus type, and generate a control signal to control the laser system 202 to deliver laser energy to the target structure 122 in accordance with the adjusted irradiation parameter setting.

In some examples, the laser controller 260 may determine the operating mode of the laser system 202 based on the classification of the target structure 122 as one of a plurality of tissue types, such as renal tissue at different anatomical locations (e.g., calyx tissue, cortex tissue, medulla tissue, or ureter tissue, as shown in FIG. 3B), normal or abnormal tissue (e.g., cancerous tissue), treatment area (e.g., tumor or polyp intended for removal) or a non-treatment area (e.g., blood vessels, muscle, etc.). The laser controller 260 may adjust the irradiation parameter setting based on the classification of tissue type, and generate a control signal to the laser system 202 that delivers laser energy to the identified anatomical structure in accordance with the adjusted irradiation parameter setting.

In some examples, irradiation parameter settings may be determined respectively for a plurality of calculi types and/or for a plurality of tissue types. A calculi type-irradiation parameter setting correspondence, or a tissue type-irradiation parameter setting correspondence, may be created and stored in the memory 250, such as in a lookup table, an associative array, or the like. The laser controller 260 may use one of such stored correspondence to determine an irradiation parameter setting that corresponds to the classified calculus type or the classified tissue type.

In various examples, the feedback analyzer 240 may continuously monitor the target structure 122, collect and analyze feedback signals, and continuously communicate with the laser controller 260. Accordingly, the laser controller 260 may continue maintaining the laser systems in one or more states until a change in the feedback is detected (e.g., a different category of the target structure 122, a different tissue type, or a different calculus type). When a change in feedback is detected, the laser controller 260 may communicate with the one or more laser systems and change their state(s) to deliver a desired therapeutic effect. Alternatively or additionally, the laser controller 260 may communicate with an operator (e.g., healthcare professional), and display one or more output(s) via one or more output system(s) indicative of the feedback signal, and may, optionally, instruct the operator to perform one or more treatment procedures with the first laser system and/or the second laser system to deliver a desired therapeutic effect.

In illustrative examples described herein, the laser controller 260 may control more than one laser system by changing the operating state of each laser system. According to an aspect, the laser controller 260 may independently control each laser system. For instance, the laser controller 260 may send a distinct control signal to each laser system to control each laser system independently of the other laser systems. Alternatively, the laser controller 260 may send a common signal to control one or more laser systems.

The laser feedback control system 200 may be in operative communication with an output systems 270. The output system 270 may communicate with and/or deliver signals received and information produced by the feedback analyzer 240 to users and/or to other systems such as an irrigation suction/pumping system used for a therapeutic treatment, or an optical display controller, or other systems. Examples of the signals and information delivered may include one or more of the feedback signal 130 (e.g., spectroscopic signals reflected from the target tissue or calculi), the spectroscopic properties generated by the to the spectroscopic sensor 242 or optionally imaging properties generated by the optional imaging sensor 244, identification of the target structure 122 generated by the target detector 246, or classification of the target structure 122 generated by the target classifier 248. In an example, the output system 270 may include a display 272, such as a screen (e.g., a touchscreen), or in the alternative, a visual indicator (e.g., LED lights of one or more colors). In an example, the output system 270 may include an auditory output systems 274 capable of providing auditory signals (e.g., speakers, an alarm system and the like). The output system 270 may provide one or more outputs (e.g., LED lights of a first color, a first message on the screen, an alarm sound of a first tone) to indicate that a desired therapeutic effect (e.g., ablation of calculi structures such as kidney stones, or carbonation of abnormal tissue such as cancerous tissue) has been achieved. In some examples, the output system 270 may provide one or more different outputs when desired therapeutic effects have not been achieved. For instance, output system 270 may provide one or more outputs (e.g., LED lights of a second color, a second message on the screen, an alarm sound of a second tone) to indicate that a desired therapeutic effect has not been achieved. In some examples, therapeutic effects on different identified structure categories (e.g., calculi versus anatomical structures) or different classified structure types (e.g., different types of calculi as show in FIG. 3A, or different types of tissue as shown in FIG. 3B) may be indicated on the output system 270 using respectively different outputs (e.g., LED lights of different colors, different messages on the screen, or different tones of alarm). Such outputs may prompt the operator (e.g., a health care professional) to take proper actions such as providing additional treatment using the one or more laser systems.

Figure 4A:
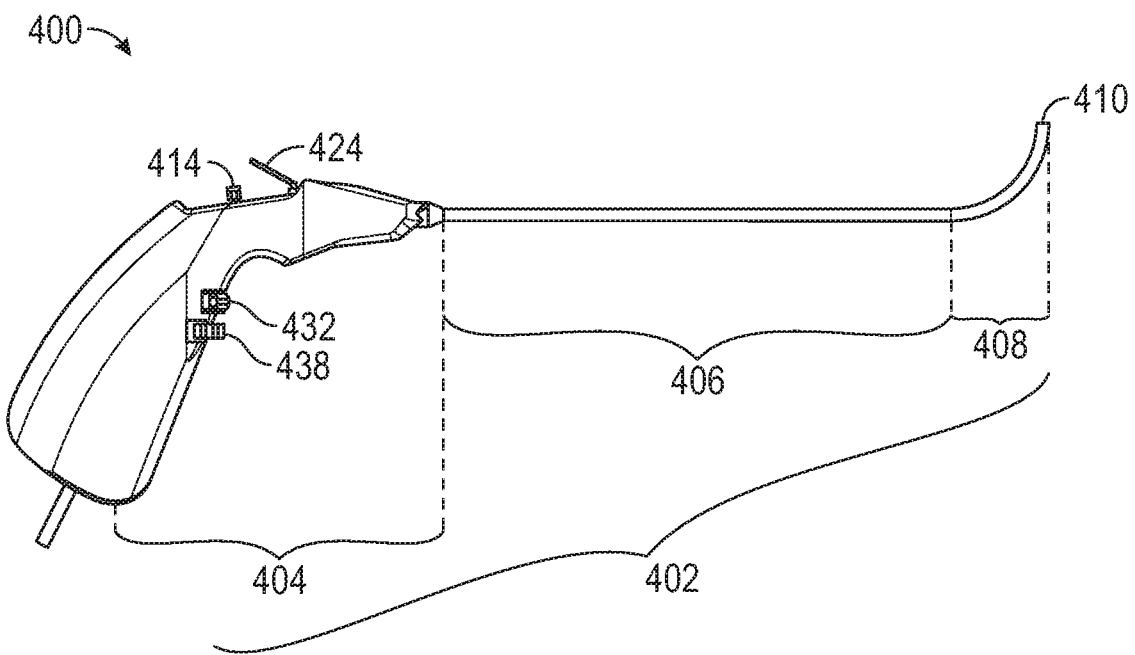
FIGS. 4A-4C are diagrams illustrating an example of an endoscope configured to provide feedback-controlled laser therapy.
Figure 4B:
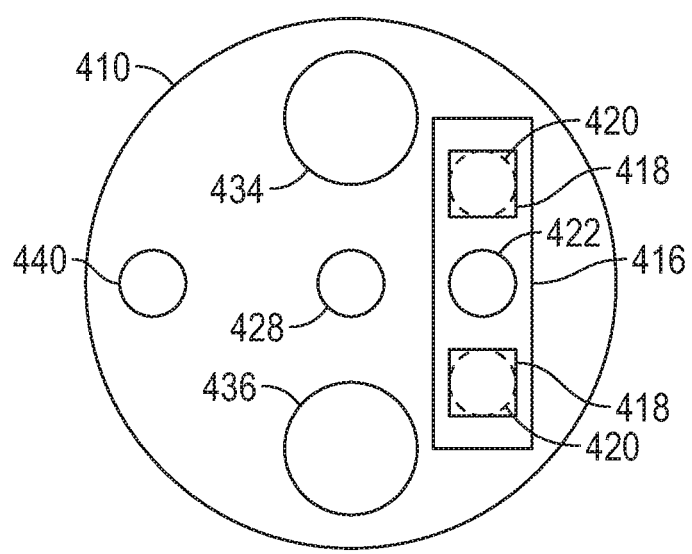

According to an aspect of the present document, the laser feedback control system 101, or a variant thereof such as the laser feedback control system 200, may be at least partially implemented in endoscope used in a medical procedure to break and remove calculi (e.g., kidney or pancreobiliary or gallbladder stones or stone fragments) or anatomical structures such as tumor tissue. A laser lithotripsy procedure may be formed through the nephroscope. FIG. 4A illustrates a side view of an exemplary endoscope 400. FIG. 4B illustrates an end-on view of the distal tip of the endoscope 400. Examples of the endoscope 400 may include a nephroscope, a cystoscope, a ureteroscope, among other varieties of endoscopes with distinct applications. The endoscope includes a body 402 at least partially insertable into a kidney of a patient. The body 402 can include a handle, a hub, or other grippable proximal portion 404, an elongate rigid portion 406 extending from the grippable proximal portion 404, and a flexible distal portion 408 extending distally from the elongate rigid portion 406 to a distal end 410. An articulation controller 414 can be located on the grippable proximal portion 404. The articulation controller 414 can be actuatable by a thumb of the human hand when the human hand grips the grippable proximal portion 404. The articulation controller 414 can adjust the position of the flexible distal portion 408. Also located on the grippable proximal portion 404 may include an electrical port 424 that may be coupled to (e.g., via one or more wires 126 extending along the body 402) a substrate 416 (as shown in FIG. 4B) located on the distal end 410 of the body 402. The substrate 416 can include one or more of a circuit board, a hybrid chip, a ceramic component, or other suitable components or elements. The electrical port 424 can receive electrical power to power the circuit board on the substrate 416. The substrate 416, such as the circuit board, can communicate digital video signal wirelessly to a display device that is external to the endoscope 400, such as a user device, a display, a computer monitor, a heads-up display, a wearable display, a virtual reality display, an augmented reality display, and others.

An optical fiber 428 (as shown in FIG. 4B), which is an example of the first optical pathway 108 of FIG. 1, may be integrated into the endoscope 400. For example, the optical fiber 428 may extend along a working channel in the body 402 of the endoscope 400. In some examples, the optical fiber 428 may be separate from the endoscope. For example, the optical fiber 428 may be fed along a working channel of the endoscope prior to use, and retrieved from a working channel of the endoscope after use.

The optical fiber 428 may be coupled to a laser or laser emitter external to the endoscope 400 via a suitable connector, and deliver laser beam to the target structure, such as a calculus structure, to ablate it into stone fragments. The laser beam generated by the laser emitter may have a wavelength that corresponds to a spectral peak of absorption of human blood and saline, such as 2100 nm, 1942 nm, and others. For example, wavelengths in the range between 1900 nm and 3000 nm may correspond to a spectral region in which water is absorbing, while wavelengths between 400 nm and 520 nm may correspond to a spectral region in which oxy-hemoglobin and/or deoxy-hemoglobin is absorbing. For example, a thulium fiber laser can produce laser beam at a wavelength of 1908 nm or 1940 nm, a thulium:YAG laser can produce laser beam at a wavelength of 2010 nm, a holmium:YAG laser can produce laser beam at a wavelength of 2120 nm, and an erbium:YAG laser can produce laser beam at a wavelength of 2940 nm. Other wavelengths in these ranges can also be used. In general, delivering laser beam that has significant absorption in blood and saline can be beneficial, because such laser beam can be minimally invasive on surrounding tissue, which can reduce or eliminate damage to the tissue at or near the calculus structure. The laser can provide light having an output power that falls within a suitable range of output power, such as between 20 watts and 120 watts, between about 20 watts and about 120 watts, and others. These ranges of output power are mere examples, and other suitable output powers or ranges of output power can also be used. The optical fiber 428 can be a multi-mode fiber or a single-mode fiber.

A laser controller 432 can be located on the grippable proximal portion 404. The laser controller 432 can toggle a state of the laser beam between an operational state ("on") and a non-operational state ("off"). For example, the laser controller 432 can direct a wired and/or wireless signal to a laser that is located external to the endoscope 400. The signal can turn on or turn off the laser. In some implementations, a practitioner can adjust one or more settings of the laser, such as the output power, on a housing of the laser. In some implementations, the practitioner can adjust one or more settings of the laser via the laser controller 432.

During a typical procedure, the practitioner can manipulate the laser controller 432 such that the laser can be operational for a period of time, such as one minutes, two minutes, three minutes, four minutes, or any suitable length of time. During the period of time of laser operation, the practitioner can manipulate the body 402 to move the delivered laser beam across a surface of the calculus structure. In some examples, the laser power level and the exposure times are such that the practitioner can safely switch the laser power on and off by hand, without a need for a mechanized or automated exposure mechanism. The laser power may also be low enough such that incidental exposure of surrounding tissue may not damage the tissue.

The practitioner can ablate the calculus structure by dusting the surface of the calculus structure. Dusting can wear down the calculus structure in a controlled manner, and can produce stone particles that can be smaller than stone fragments obtained from fragmenting or fracturing the calculus structure. For example, a typical kidney stone can be sized between about 1 mm and about 20 mm Fragmenting or fracturing the kidney stone can produce kidney stone fragments that can be sized smaller than the size of the stone, such as between a few mm and less than about 10 mm in size. Dusting of the kidney stone can produce kidney stone particles that can be smaller than about 1 mm in size.

To remove calculi or stone fragments, the practitioner can use a stone retrieval device, such as a basket, that can pass through an orifice in the endoscope 400. The practitioner can use the stone retrieval device to select and remove individual fragments. In addition to, or instead of, the stone retrieval device, the endoscope 400 can include a flushing system to flush away the stone fragments. The flushing system may include a flushing controller 438 located on the grippable proximal portion 404, and can operatively control a flow of irrigation fluid through an irrigation lumen 434 and suction of fluid and waste through a suction lumen 436.

The endoscope 400 can optionally include a tube, chamber, additional working channel, or other passage 440 within a body of the endoscope 400. A practitioner can use the passage 440 to deploy a separate tool or instrument, such as a lithotripter, a stone retrieval basket, or another suitable tool or instrument.

The endoscope 400 can include a visualization system at the distal end 410 of the body 402 to allow an operator to visualize the stone fragments. The visualization system can illuminate a working area of calculi (e.g., kidney or pancreobiliary or gallbladder stones) and can generate a video image or one or more static images of the illuminated area of the calculi. The visualization system can direct the video image to a display, such as the video monitor. The display can be external to the endoscope 400 and can be viewable during the calculi removal procedure.

The visualization system can include at least one light source 418 located on the substrate 416. The substrate 416 can be a circuit board that mechanically supports and electrically powers the light source 418. Examples of the light source 418 may include light-emitting diode (LED), xenon light, among others. In an example, the light source 418 can emit light distally away from the distal end 410 of the body 402 to illuminate the calculi. In some examples, an external light source (e.g., outside of the endoscope 400) may be used to provide light transmitted through the body 402 (such as via an optical pathway therein) to illuminate the calculi. The light source 418 can emit white light to illuminate the calculi. White light can allow the practitioner to observe discolorations or other color-based effects on the calculi or on the tissue proximate the distal end 410 of the body 402. The light source 418 can emit blue light to illuminate the calculi. Blue light can be well-suited to show thermal tissue spread and thereby detect damage in the tissue. Other colors and/or color bands, such as red, amber, yellow, green, or others, may be used.

Each light source 418 may be coupled to an optional lens 420 (see FIG. 4B) that can angularly adjust the light output from the light source 418. The lens 420 can narrow the light output from the light source 418. The lens 420 can widen the light output from the light source 418. Such an angular adjustment can help ensure that the calculi and the tissue are sufficiently illuminated within a specified angular field of view.

The visualization system can include a camera 422 (see FIG. 4B) located on the substrate 416. The substrate 416 can be a circuit board that mechanically supports and electrically powers the camera 422. The camera 422 can capture a video image or one or more static images of the illuminated calculi. The video image can be in real-time, or nearly real-time with a relatively short latency for processing, so that the practitioner can observe the calculi and the surrounding tissue as the practitioner manipulates the body 402 and controls of the endoscope 400. The camera 422 can include a lens and a multi-pixel sensor located at a focal plane of the lens. The sensor can be a color sensor, such as a sensor that provides intensity values for red light, green light, and blue light for each pixel in the video image. The circuit board can produce a digital video signal representing the captured video image of the illuminated calculi. The digital video signal can have a video refresh rate of 10 Hz, 20 Hz, 24 Hz, 25 Hz, 30 Hz, 40 Hz, 50 Hz, 60 Hz, or another suitable video refresh rate.

Figure 4C:
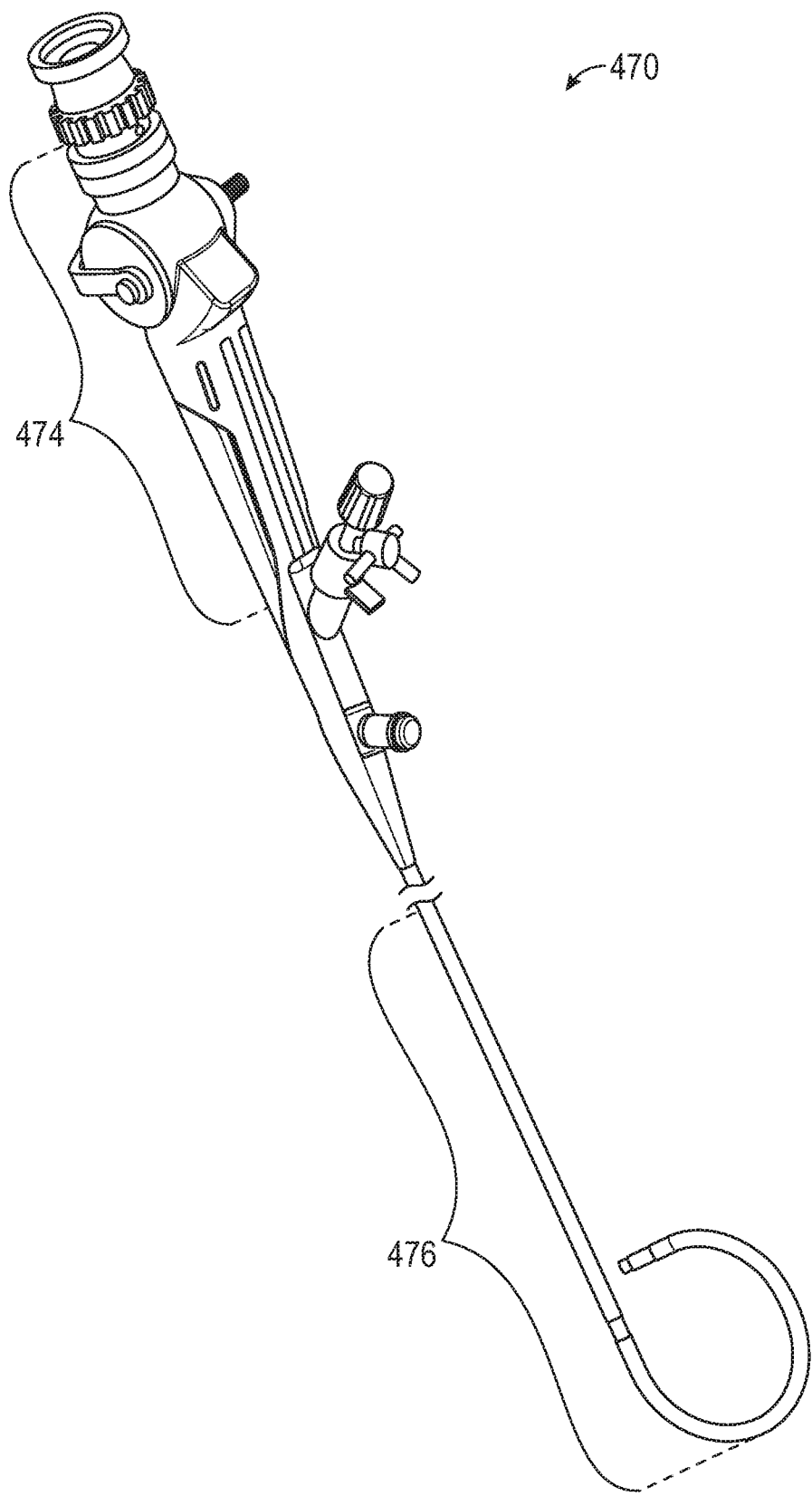

FIG. 4C illustrates another example of an endoscope that may be used in ureteroscopy procedures, also known as a ureteroscope 470. Similar to the endoscope 400, the ureteroscope 470 may be used for providing feedback-controlled laser therapy. The ureteroscope 470 includes a grippable proximal portion 474 different from the grippable portion 404 of the endoscope 400. The ureteroscope 470 may include a slim elongate shaft 476 that helps scope insertion into smaller ureters and maximizes visualization when used with an access sheath.

FIGS. 5-9 illustrated various examples of an endoscope and its use in a feedback-controlled laser treatment system, such as the laser treatment system 100. FIG. 5A is a cutaway drawing of an elongate body portion of an exemplary endoscope 510 that encompasses various components, and FIG. 5B is a cross-sectional view of the elongate body of the endoscope 510. The endoscope 510 may include a laser fiber 512, an illumination light 514, and a camera 516. The laser fiber 512 is an example of the optical pathway 108 of the laser system 102 or the laser system 202. The laser fiber 512 may extend along a working channel 513 within the elongate body of the endoscope 510. In some examples, the laser fiber 512 may be separate from the endoscope. For example, the laser fiber 512 may be fed along a working channel of the endoscope prior to use, and retrieved from a working channel of the endoscope after use.

The illumination light 514 may be a part of a visualization system that allows an operator to visualize the target structure (e.g., tissue or calculi structures). Examples of the illumination light can include one or more LEDs configured to emit light distally away from the distal end of the elongate body of the endoscope to illuminate the field of the target structure. In an example, the illumination light 514 may emit white light to illuminate the target structure. White light can allow the practitioner to observe discolorations or other color-based effects on the calculi or on the tissue proximate the distal end of the body of the endoscope. In an example, the illumination light 514 may emit blue light to illuminate the target structure. Blue light can be well-suited to show thermal tissue spread and thereby detect damage in the tissue. Other colors and/or color bands, such as red, amber, yellow, green, or others, can also be used.

The camera 516 is a part of the visualization system. The camera 516 is an example of the imaging sensor 244. The camera 516 can capture a video image or one or more static images of the illuminated target structure and the surrounding environment. The video image can be in real-time, or nearly real-time with a relatively short latency for processing, so that the practitioner can observe the target structure as the practitioner manipulates the endoscope. The camera 516 can include a lens and a multi-pixel sensor located at a focal plane of the lens. The sensor can be a color sensor, such as a sensor that provides intensity values for red light, green light, and blue light for each pixel in the video image. The circuit board can produce a digital video signal representing the captured video image of the illuminated calculi. The digital video signal can have a video refresh rate of 10 Hz, 20 Hz, 24 Hz, 25 Hz, 30 Hz, 40 Hz, 50 Hz, 60 Hz, or another suitable video refresh rate.

FIG. 6 illustrates an example of a laser treatment system 600 including an endoscope 510 integrated with a feedback-controlled laser treatment system 610 that receives camera feedback. The laser treatment system 600, which is an example of the laser treatment system 100, comprises the endoscope 510, the feedback-controlled laser treatment system 610, a laser source 620, and a light source 630. In various examples, a portion or the entirety of the feedback-controlled laser treatment system 610 may be embedded into the endoscope 510.

The feedback-controlled laser treatment system 610, which is an example of the laser feedback control system 200, includes a spectrometer 611 (an example of the spectroscopic sensor 242), a feedback analyzer 612 (an example of at least a portion of the feedback analyzer 240), and a laser controller 613 (an example of the laser controller 260). The laser source 620 is an example of the laser system 202, and can be coupled to the laser fiber 512. Fiber integrated laser systems may be used for endoscopic procedures due to their ability to pass laser energy through a flexible endoscope and to effectively treat hard and soft tissue. These laser systems produce a laser output beam in a wide wavelength range from UV to IR area (200 nm to 10000 nm). Some fiber integrated lasers produce an output in a wavelength range that is highly absorbed by soft or hard tissue, for example 1900-3000 nm for water absorption or 400-520 nm for oxy-hemoglobin and/or deoxy-hemoglobin absorption. Table 1 above is a summary of IR lasers that emit in the high water absorption range 1900-3000 nm.

Some fiber integrated lasers produce an output in a wavelength range that is minimally absorbed by the target soft or hard tissue. These types of lasers provide effective tissue coagulation due to a penetration depth that similar to the diameter of a small capillary 5-10 μm. Examples of laser source 620 may include UV-VIS emitting $I_xGa_{1-x}N$ semiconductor lasers such as GaN laser with emission at 515-520 nm, $In_xGa_{1-x}N$ laser with emission at 370-493 nm, $Ga_xAl_{1-x}As$ laser with emission at 750-850 nm, or $In_xGa_{1-x}As$ laser with emission at 904-1065 nm, among others.

The light source 630 may produce an electromagnetic radiation signal that may be transmitted to the target structure 122 via a first optical pathway extending along the elongate body of the endoscope. The first optical pathway may be located within the working channel 513. In an example, the first optical pathway may be an optical fiber separate from the laser fiber 512. In another example, as illustrated in FIG. 6, the electromagnetic radiation signal may be transmitted through the same laser fiber 512 used for transmitting laser beams. The electromagnetic radiation exits the distal end of the first optical pathway and projects to the target structure and surrounding environment. As illustrated in FIG. 6, the target structure is within the view of the endoscopic camera 516, such that in response to the electromagnetic radiation projecting to the target structure and surrounding environment, the endoscopic camera 516 (such as a CCD or CMOS camera) may collect the signal reflected from target structure 122, produce an imaging signal 650 of the target structure, and deliver the imaging signal to the feedback-controlled laser treatment system 610.

In addition to or in lieu of the feedback signal (e.g., imaging signal) generated and transmitted through the camera system 516, in some examples, the signal reflected from the target structure may additionally or alternatively be collected and transmitted to the feedback-controlled laser treatment system 610 through a separate fiber channel or a laser fiber such as associated with the endoscope 510. FIG. 7 illustrates an example of a laser treatment system 700 including the endoscope 510 integrated with the feedback-controlled laser treatment system 610 configured to receive spectroscopic sensor feedback. A reflected spectroscopic signal 750 (which is an example of the feedback signals 130 of FIGS. 1 and 2) may travel back to the feedback-controlled laser treatment system 610 through the same optical pathway, such as the laser fiber 512, that is used for transmitting the electromagnetic radiation from the light source 630 to the target structure. In another example, the reflected spectroscopic signal 750 may travel to the feedback-controlled laser treatment system 610 through a second optical pathway, such as a separate optical fiber channel from the first optical fiber transmitting the electromagnetic radiation from the light source 630 to the target structure.

The feedback-controlled laser treatment system 610 may analyze one or more feedback signals (e.g., the imaging signal 650 of the target structure or the reflected spectroscopic signal 750) to determine an operating state for the laser source 620. The spectrometer 611 may generate one or more spectroscopic properties from the one or more feedback signals, such as by using one or more of a FTIR spectrometer, a Raman spectrometer, a UV-VIS spectrometer, a UV-VIS-IR spectrometer, or a fluorescent spectrometer, as discussed above with reference to spectroscopic sensor 242. The feedback analyzer 612 may be configured to identify or classify the target structure as one of a plurality of structure categories or structure types, such as by using one or more of the target detector 246 or the target classifier 248. The laser controller 613 may be configured to determine an operating mode of the laser system 620, as similarly discussed above with reference to FIG. 2.

The light source 630 may produce electromagnetic radiation within an optical range from UV to IR. Table 2 below presents examples of light source 630 for the spectroscopic system as applicable to the examples discussed herein.

TABLE 2

Light sources for spectroscopic system

| Application | Wavelength Range | Type |
| --- | --- | --- |
| Color/VIS/NIR | 360-2500 nm | Tungsten Halogen |
| DUV | 190-400 nm | Deuterium |
| UV | 215-400 nm | Deuterium |
| UV/VIS/NIR reflection/absorption | 215-2500 nm | Deuterium/Halogen |

TABLE 2-continued

Light sources for spectroscopic system

| Application | Wavelength Range | Type |
| --- | --- | --- |
| UV/VIS/NIR absorption | 200-2500 nm | Deuterium/Halogen |
| UV/VIS | 200-1000 nm | Xenon |
| FTIR | 2000-25000 nm | Silicon Carbide |
| UV/VIS/IR Fluorescence | Multiple narrow emitting | LED, Laser Diode |

In some examples, the feedback analyzer 612 may determine a distance 660 (as shown in FIG. 6) between the distal end of the laser fiber 512 and the target structure 122, or between the distal end of the optical pathway for receiving and transmitting the reflected signal back to the spectrometer 611 and the target structure 122. The distance 660 may be calculated using a spectroscopic property, such as a reflectance spectrum, produced by the spectrometer 611. The laser controller 613 may control the laser source 620 to deliver laser energy to the target structure 122 if the distance 660 satisfies a condition, such as falling below a threshold ($d_{th}$) or within a specified laser firing range. In an example, if the target structure 122 is identified as an intended treatment structure type (e.g., a specified soft tissue type or a specified calculus type) but the target structure 122 is not within the range of the laser (e.g. $d>d_{th}$), the laser controller 613 may produce a control signal to "lock" the laser source 620 (i.e., preventing the laser source 620 from firing). Information about the distance 660 and an indication of the target structure being out of the range of laser ($d>d_{th}$) may be presented to the practitioner, who may then adjust the endoscope 510 such as repositioning the distal end of the laser fiber 512 to move to closer to the target. The distance 660, as well as the target structure type, may be monitored and determined continuously and presented to the practitioner. When the target is recognized as the intended treatment structure type, and is within the range of laser ($d<=d_{th}$), the laser controller 613 may produce a control signal to "unlock" the laser source 620, and the laser source 620 may aim and fire at the target structure 122 in accordance with the laser operating mode (e.g., power setting). Examples of methods for calculating the distance 660 from spectroscopic data are discussed below, such as with reference to FIG. 10.

In some examples, the spectrometer 611 may be configured to generate the spectroscopic properties (e.g., reflectance spectra) further using information about geometry and positioning of the optical pathway configured to transmit the electromagnetic radiation from the light source to the target. For example, an outer diameter of the laser fiber 512 or an outer diameter of a separate optical pathway for transmitting the spectroscopic signal reflected from the target to the spectrometer 611, or an angle of protrusion of said fiber or pathway from the endoscope 510, may affect the intensity of reflected signal. The outer diameter and/or the protrusion angle may be measured and provided to the spectrometer 611 to obtain the reflectance spectra data. The distance 660 between the target structure and the distal end of the fiber, as discussed above, may be calculated using the spectra data, the measured outer diameter of the fiber or optical pathway and its angle of protrusion, and/or input signals from the endoscopic image processor.

Figure 8A:
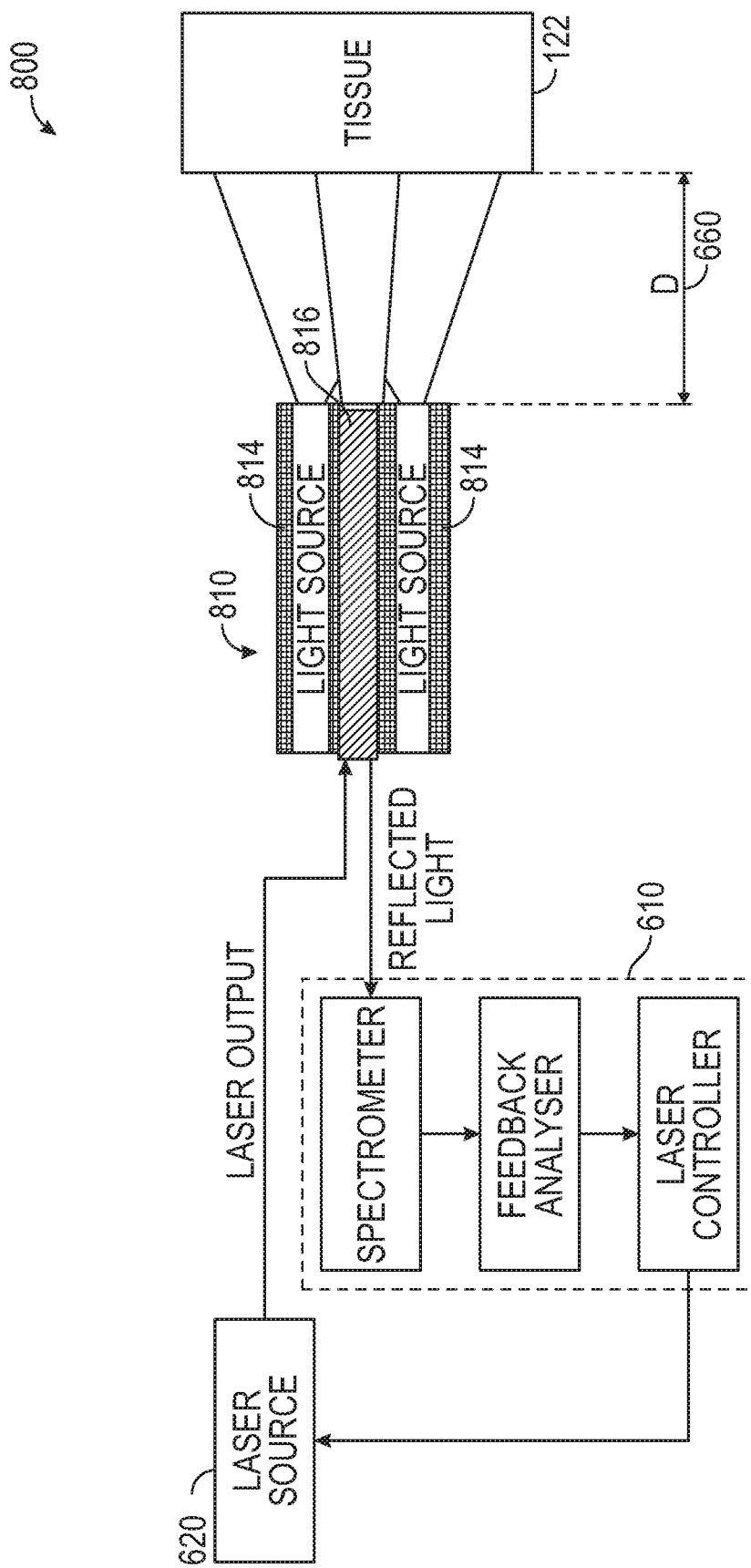
FIGS. 8A-8C illustrate an example of a laser treatment system including an endoscope with an integrated multi-fiber accessory.
Figure 8C:
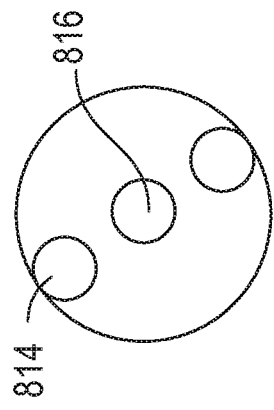
Figure 8B:
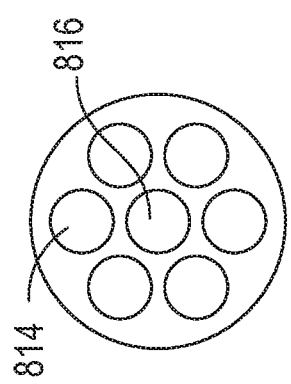

FIGS. 8A-8C illustrate a laser treatment system 800 comprising an endoscope 810 with an integrated multi-fiber accessory, and a surgical laser system comprising the feedback-controlled laser treatment system 610 and the laser source 620. The multi-fiber accessory includes an optical pathway 816 used for transmitting the spectroscopic signal back to the spectrometer 611, as well as for delivering surficial laser energy from the laser source 620 to the target structure. The laser controller 613 may control the timing of the laser firing such that the transmission of spectroscopic signal and delivery of laser energy may occur at different time. The multi-fiber accessory also includes a plurality of light source fibers 814 embedded into, and extending along an elongate body of, the endoscope 810. By way of example and not limitation, FIG. 8B illustrates six light source fibers 814 radially distributed surround the optical pathway 816, such as along a circumference with respect to the optical pathway 816 on the radial cross-section of the elongate body of the endoscope. In the example as shown in FIG. 8B, the optical pathway 816 may be located at substantially the central longitudinal axis of the elongate body of the endoscope 810. Other number of light source fibers, and/or other positions of the light source fibers relative to the optical pathway 816, may be used. For example, FIG. 8C illustrates two light source fibers 814 radially positioned at opposite sides of the optical pathway 816.

Figure 5A:
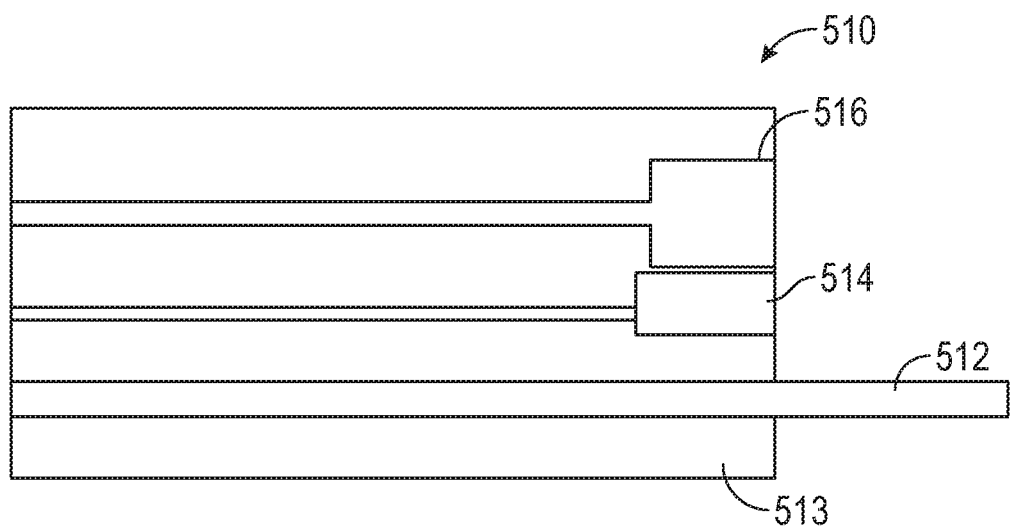
FIG. 5A-5B are diagrams illustrating a portion of an exemplary endoscope configured to provide feedback-controlled laser therapy.
Figure 5B:
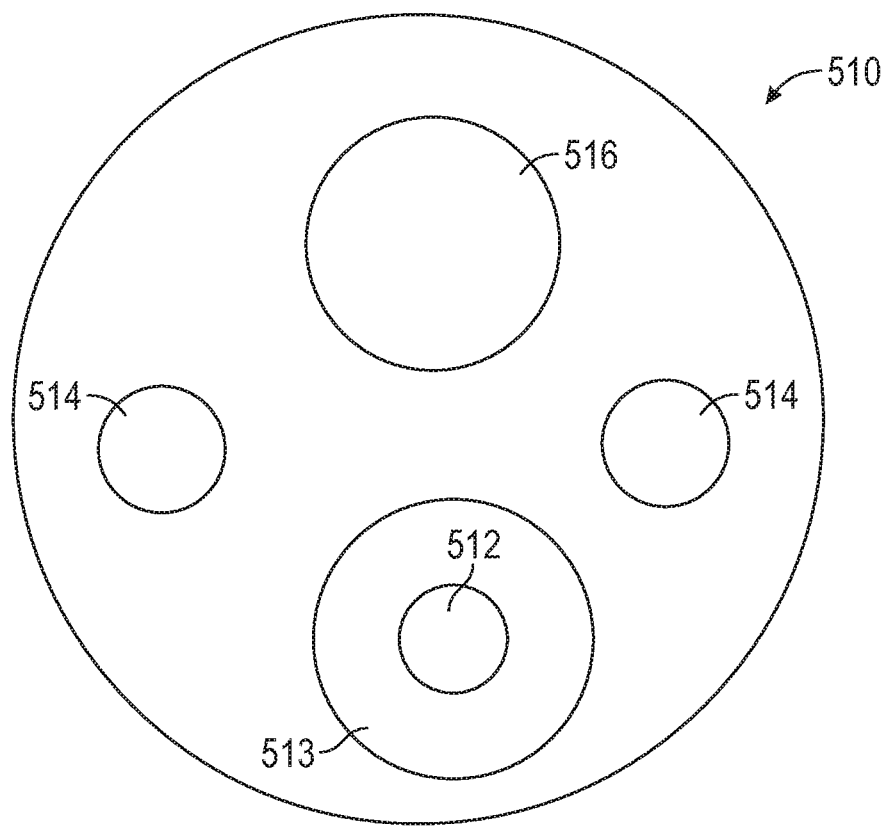

The light source fibers 814 may be coupled to the light source 630 as discussed above with reference to FIGS. 6-7. Alternatively, the light source fibers 814 may be coupled to the illumination light 514 as shown in FIG. 5A-5B. Light from the endoscope light source, either the illumination light 514 (e.g., one or more LEDs) or the remote light source 630 such as external to the endoscope, may serve the functions of illuminating the target and producing spectroscopic signal reflected from the target surface which may be collected for spectroscopic analysis. The feedback analyzer 612 may determine the distance 660 between the distal end of the endoscope 810 and the target structure 122, as similarly shown in FIGS. 6-7.

Figure 9:
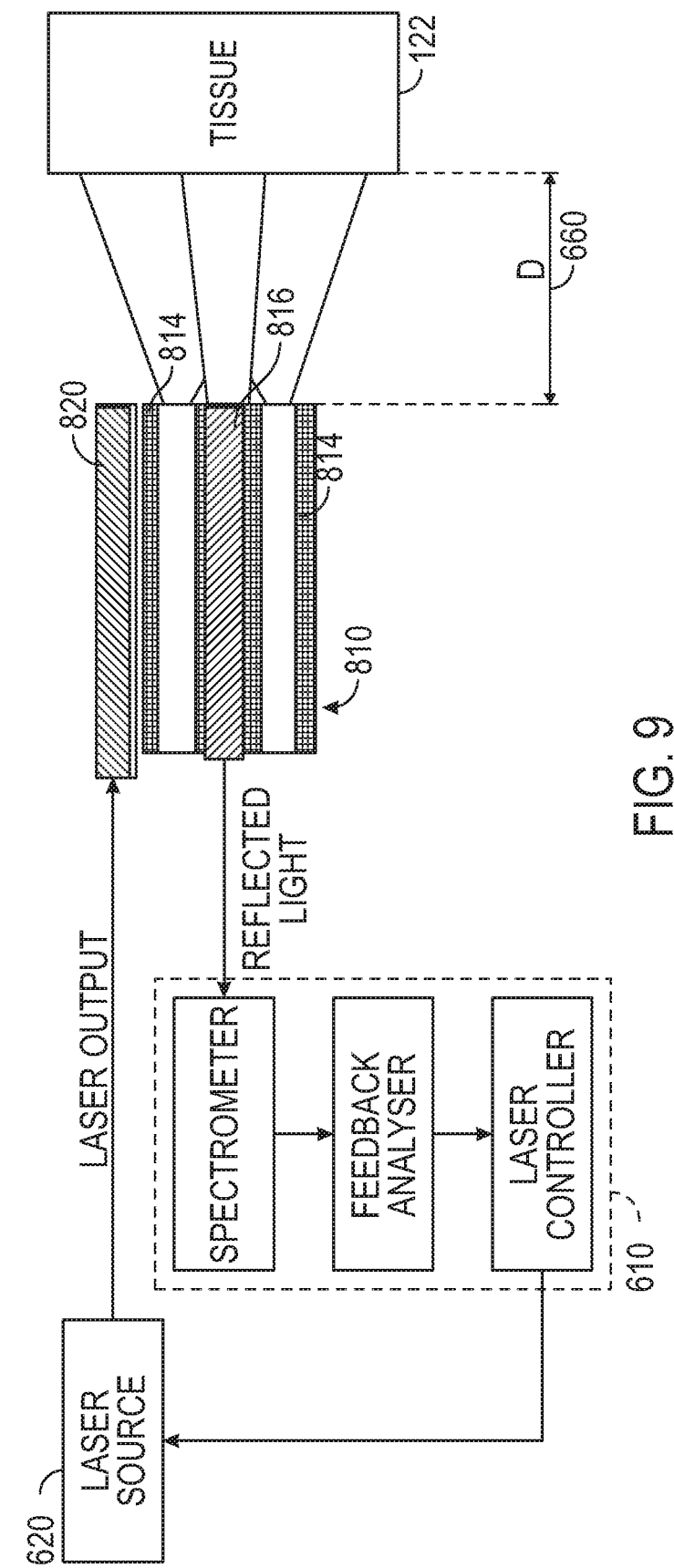
FIG. 9 illustrate a laser treatment system including a dedicated spectroscopy signal fiber and a separate surgical laser fiber.

FIG. 9 illustrate a laser treatment system 900, which is a variant of the illustrate a laser treatment system 800. Instead of delivering laser energy through the optical pathway 816, a separate surgical laser fiber 820 may be used for delivering surficial laser energy from the laser source 620 to the target structure. The optical pathway 816 is used as a dedicated spectroscopy signal fiber for transmitting the spectroscopic signal back to the spectrometer 611.

Figure 10:
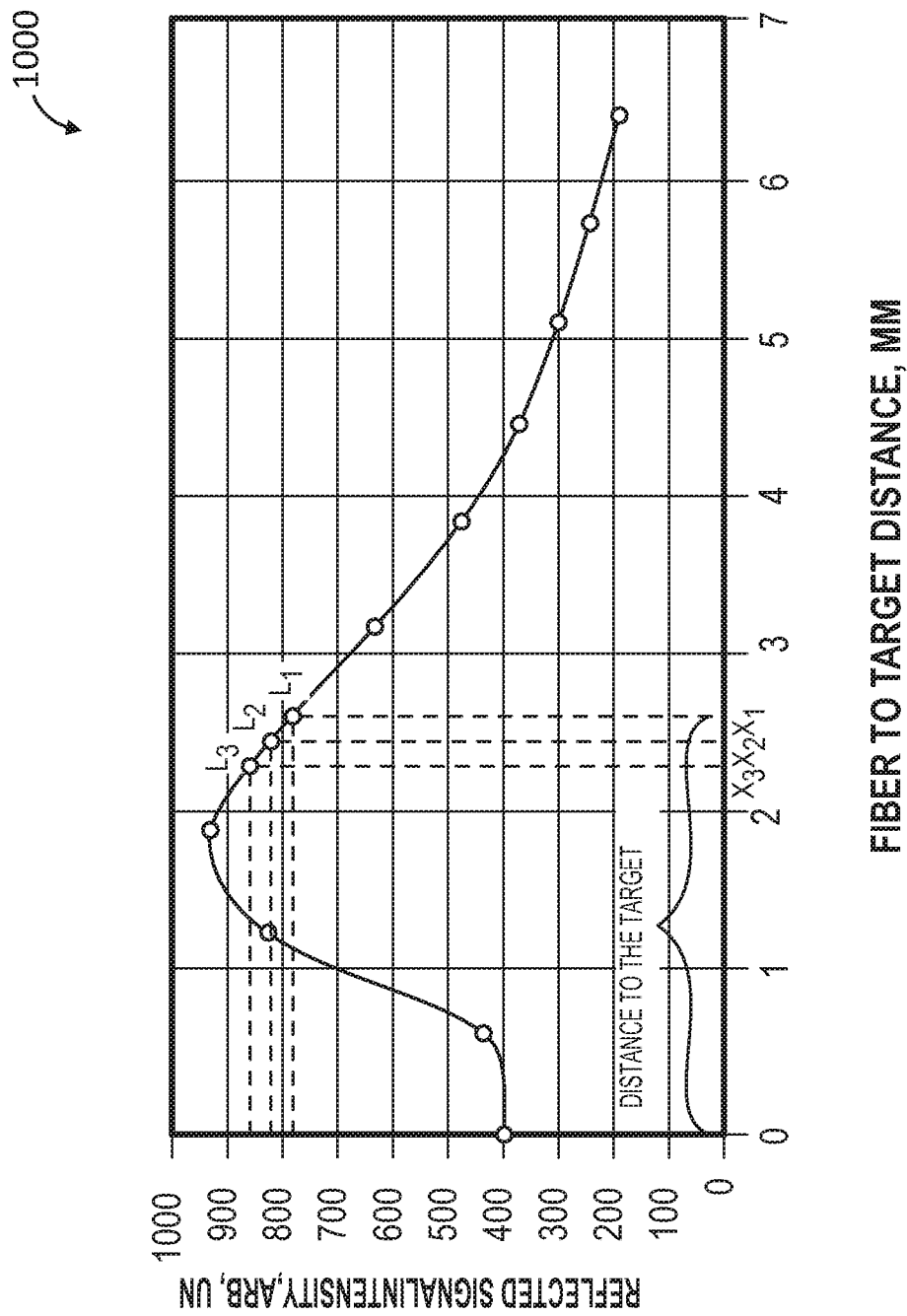
FIG. 10 illustrates an example of a calibration curve representing a relationship between a spectroscopic reflected signal intensity and the distance between a distal end of a fiber and a target structure using the feedback signal reflected from the target structure.

FIG. 10 is a diagram illustrating a calibration curve 1000 representing a relationship between a spectroscopic reflected signal intensity spectroscopic signal reflected from the target structure in response to the electromagnetic radiation) and the distance 660 between a distal end of a fiber and a target structure using the feedback signal reflected from the target structure, such as illustrated in FIGS. 6-9. The calibration curve 1000 may be generated by measuring the reflected light intensity at different distances between the tissue and spectroscopic probe distal end when the target structure is projected by electromagnetic radiation at a specific wavelength (e.g., 450 nm or 730 nm). By referencing the calibration curve, analyses of a spectroscopic signal allow quick estimation of the distance.

An exemplary process of generating the calibration curve is as follows. First, reference value for each distance may be calculated. The calibration curve itself may not be used for identifying the distance, because light reflection intensity depends of the reflectance of specimen or so on. One example of reference value to cancel the effect of reflectance of specimen is as follows:

$$\text{Reference value} = dI/dx * 1/I \quad (1)$$

During an in vivo surgery process, an operator may move the fiber or endoscope with continuous recording of the spectroscopic feedback until the reflection spectra of the target tissue composition can be detected.

Referring to FIG. 10, a first spectrum may be measured at distance $x_1$ where the reflected light intensity is $I_1$. At this timing, actual value of $x_1$ and curve of reflected signal intensity is unknown. Then, the fiber or endoscope distal end (reflected light detector) may be moved continually, and the next reflection light intensity $I_2$ corresponding the distance $x_2$ may be measured. $x_2$ may be close to $x_1$, such that the curve between $x_1$ and $x_2$ may be approximated as linear. At this timing, $x_1$, $x_2$ and curve of reflected signal intensity is unknown. A compared value may be calculated using $I_1$, $I_2$ and delta $(x_2-x_1)$, as follows:

$$\text{Compared value} = \text{delta}(I_2-I_1)/\text{delta}(x_2-x_1) * 1/I_1 \quad (2)$$

Then, the reference values are searched for one that is identical to the compared value. If there is only one reference value $(x_r)$ found to be identical to the compared value given in Equation (2), then $x_r$ can be determined as distance of $x_1$. If there are two reference values $(x_{r1}, x_{r2})$, then the fiber or endoscope distal end (reflected light detector) may be continued to move, and the next reflection light intensity $I_3$ corresponding the distance $x_3$ may be measured. $x_3$ may be close to $x_1$, so that the curve between $x_2$ and $x_3$ may be approximated as linear. At this timing, $x_1$, $x_2$, $x_3$ and curve of reflected signal intensity is unknown. A new compared value can be calculated as follows using $I_1$, $I_2$, $I_3$, delta $(x_2-x_1)$, and delta $(x_3-x_2)$.

$$\text{Compared value} = \text{delta}(I_3-I_2)\text{delta}(x_3-x_2) * 1/I_2 \quad (3)$$

Then, the reference values are searched for one that is identical to $x_{r1}$ delta $(x_2-x_1)$ and $x_{r2}$ delta $(x_2-x_1)$. The references values can be compared to the compared value given in Equation (3). The distance whose reference value is more similar to the compared value is estimated as actual distance.

During in vivo surgery process, an example method may comprise moving the fiber or endoscope with continuous recording of the spectroscopic feedback until the reflection spectra of the target composition will be detected. With the major case when the spectroscopic distal end is moving toward the target, the intensity of the detected reflected light initially will be weak and will be increased with reducing a distance between the target and a fiber end. For example, the first spectrum was measured on distance $d_1$ where the reflected light intensity is Continued slightly moving of the fiber or endoscope distal end toward the target, with continuous collecting the reflection data, and the method may measure the next reflection light intensity 12 corresponding the distance $d_2$. The method may then comprise calculation of the value of reflected signal changes slope=delta $(I_2-I_1)$/delta$(d_2-d_1)$ [1]. To make the value of the calculated slope independent on the reflected light intensity the calculated slope may be normalized. The final formula to calculate slope of reflected light at measured distance becomes:

$$\text{Slope (normalized)} = [\text{delta}(I_2-I_1)/\text{delta}(d_2-d_1)]/I_o \quad (4)$$

where: $I_o = \text{AVERAGE}(I1 I2)$

The method may then compare the calculated slope to the one on the calibration curve in a library to allow estimating the required distance. All calculation can be done fast using software.

Figure 11:
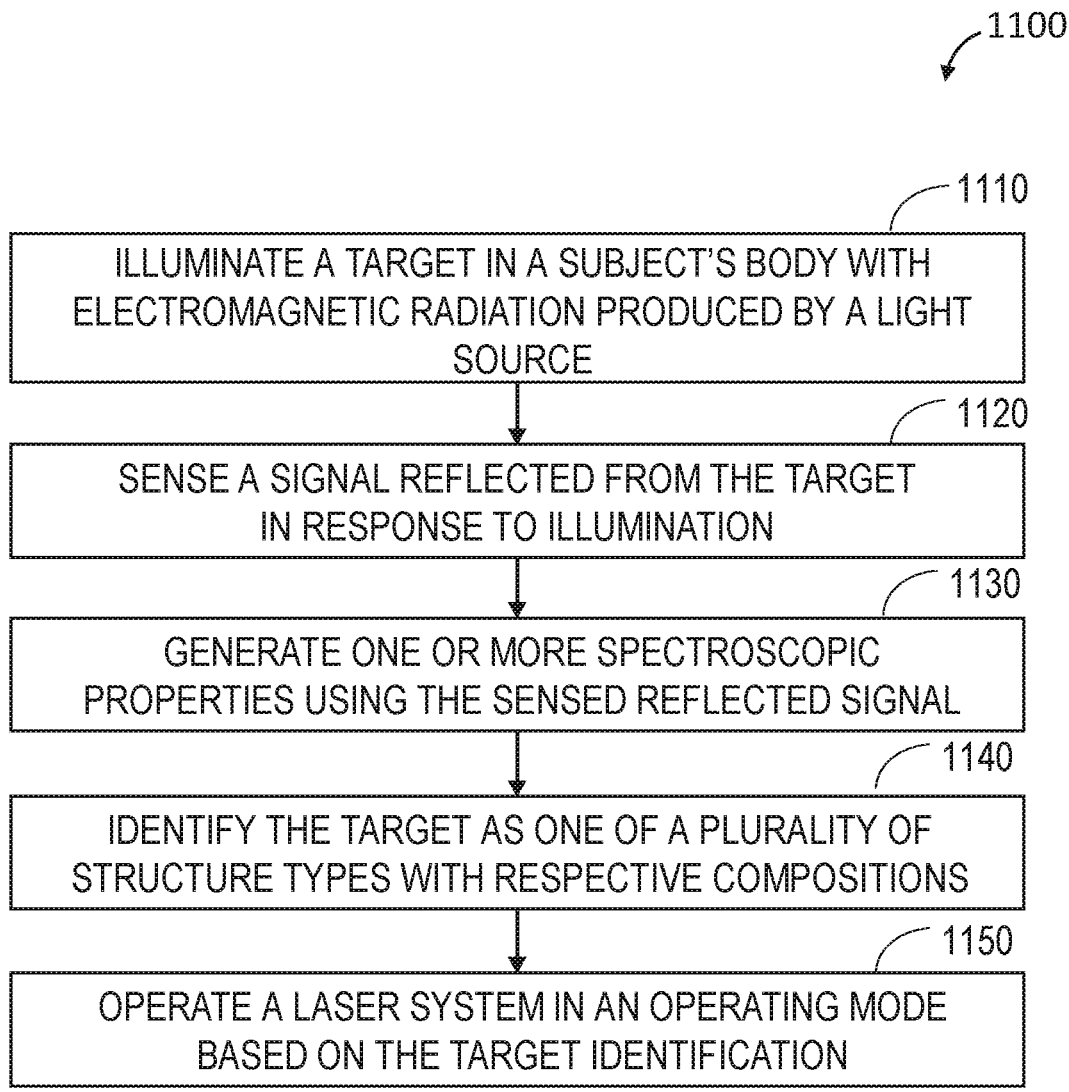
FIG. 11 a flow chart illustrating a method for controlling a laser system to deliver a laser beam to a target structure in a body of a subject, such as an anatomical structure or a calculus structure.

FIG. 11 is a flow chart illustrating a method 1100 for controlling a laser system to deliver a laser beam to a target structure in a body of a subject, such as an anatomical structure (e.g., soft tissue, hard tissue, or abnormal such as cancerous tissue) or a calculus structure (e.g., kidney or pancreobiliary or gallbladder stone). The method 1100 may be implemented in and executed by a laser treatment system, such as the laser treatment system 100 or a variant thereof, such as the laser feedback control system 200. Although the processes of the method 1100 are drawn in one flow chart, they are not required to be performed in a particular order. In various examples, some of the processes can be performed in a different order than that illustrated herein.

At 1110, a target in a subject's body is illuminated with electromagnetic radiation produced by a light source, such as the light source 630. The light source may produce electromagnetic radiation within an optical range from UV to IR. Examples of the light sources and corresponding electromagnetic radiation wavelengths are shown in Table 2 above. The electromagnetic radiation may be transmitted to the target structure via an optical pathway extending along an elongate body of an endoscope, such as discussed above with reference to FIGS. 6-9. Alternatively, the light source may include an illumination light, such as one or more LEDs of a visualization system, positioned at a distal end of an endoscope and configured to illuminate the target structure and the surrounding environment during an endoscopy procedure, as illustrated in FIGS. 5A-5B.

At 1120, a signal reflected from the target in response to the electromagnetic radiation may be sensed by a spectroscopic sensor, such as using a spectroscopic sensor 242 or a variant thereof. Examples of the spectroscopic sensor may include a Fourier Transform Infrared (FTIR) spectrometer, a Raman spectrometer, a UV-VIS spectrometer, a UV-VIS-IR spectrometer, or a fluorescent spectrometer, among others. The reflected signal may be transmitted to the spectroscopic sensor through an optical pathway, such as the signal transmission pathway 250 as shown in FIG. 2, or the optical pathway 816 as shown in FIG. 8-9. The optical pathway has optical properties suitable for transmission of spectroscopic signals reflected from the tissue to the spectroscopic sensor. Alternatively, the spectroscopic sensor may be operatively coupled to a laser fiber for transmitting laser beams, such as the first optical pathway 108 or the second optical fiber 118 as shown in FIG. 1, the laser fiber 512 shown in FIG. 6-7, or the optical pathway 816 as shown in FIG. 8A-8C.

Additionally or alternatively, the reflected signal from the target in response to the electromagnetic radiation may be sensed using one or more imaging sensor, such as the imaging sensor 244 as shown in FIG. 2. Examples of the imaging sensor may include an imaging camera, such as a CCD or CMOS camera sensitive in ultraviolet (UV), visible (VIS) or infrared (IR) wavelengths in an embodiment. The camera may be embedded in an endoscope, such as the camera 516 incorporated into the endoscope 510, as illustrated in FIGS. 5-7.

At 1130, one or more spectroscopic properties may be generated from the sensed reflected signal, such as using the feedback analyzer 240 as shown in FIG. 2, Spectroscopic properties may include characteristics such as reflectivity, reflectance spectrum, absorption index, and the like. The spectroscopic properties may be indicative of a structure category (e.g., anatomical tissue or calculi) or specific structure types indicative of chemical composition of the target structure. In an example, the spectroscopic properties may include a reflectance spectrum that represents reflectance intensities over a plurality of wavelengths. Reflectance can be determined as a fraction of incident electromagnetic power reflected at a material interface. It represents the effectiveness of the material surface in reflecting radiant energy, such as electromagnetic radiation emitted from a light source. The reflectance spectrum may be formatted as a data array or a graphical representation also referred to a spectral reflectance curve.

The spectroscopic properties may include one or more characteristic spectral features extracted from a reference spectrum. Examples of the characteristic reflectance features may include reflectance intensity (or normalized reflectance spectral intensity) at a specific wavelength or over a wavelength range, a statistical value calculated from the reflectance spectrum (e.g., a variation of reflectance over two or more different wavelengths, a rate of change of reflectance over a range of wavelengths, or the like), or a graphical feature representing the morphology of at least a portion of the spectral eflectance curve (e.g., a slope, a curvature, a segment of the curve, or the like).

In some examples, the spectroscopic properties (e.g., reflectance spectra) may be generated further using geometry and positioning information about at least one optical pathway associated with an endoscope and configured to transmit one or more of the laser beam, the signal reflected from the target, or the electromagnetic radiation produced by the light source. The geometry and positioning information may include an outer diameter of the at least one optical pathway, and/or an angle of protrusion of a distal end of the at least one optical pathway relative to the endoscope.

At 1140, based on the one or more spectroscopic properties, the target structure may be identified as one of a plurality of structure types with respective compositions, such as using the feedback analyzer 240. In an example, the target structure may be identified as a category of calculus structure or as a category of anatomical structure, such as using the target detector 246. Examples of calculus structure may include stones or stone fragments in various stone-forming regions such as urinary system, gallbladder, nasal passages, gastrointestinal tract, stomach, or tonsils. Examples of the anatomical structure may include soft tissue (e.g., muscles, tendons, ligaments, blood vessels, fascia, skin, fat, and fibrous tissues), hard tissue such as bone, connective tissue such as cartilage, among others. As discussed above with reference to FIGS. 3A-3B, calculus structures (e.g., a kidney stone) and anatomical structures (e.g., soft or hard tissue of a subject) may have distinct reflectance spectra. Spectral features extracted from the reflectance spectrum of the target structure may be used to categorize the target structure as either a calculus structure or an anatomical structure (e.g., soft or hard tissue), as described above with reference to FIGS. 2 and 3A-3B.

Additionally or alternatively, the target structure may be classified as one of a plurality of calculi types, or as one of a plurality of tissue types, such as using the target classifier 248. As illustrated in FIG. 3A-3B, different structure types within the same category (e.g., calculi category, or anatomical structures category) may demonstrate distinct reflectance properties. Such intra-category reflectance spectra differences may be used to classify the target structure as a particular structure type, such as a particular tissue type within an identified category of anatomical structure, or as a particular calculus type within an identified category of calculus structure. The classification may be based on one or more of reflectance at a specific wavelength, a statistical feature (e.g., variance or other variation metric) of reflectance over two or more different wavelengths, or a graphical feature generated from a graphical representation of the reflectance spectrum. In an example, an identified calculus target (e.g., a renal stone) may be classified as one of stone types with distinct chemical compositions, such as one of a CaP stone, a MAP stone, a COM stone, a COD stone, a cholesterol-based stone, or a uric acid (UA) stone. In an example, an identified tissue target may be classified as one of tissue types with distinct anatomical locations. For example, a renal tissue target may be classified as one of calyx tissue, cortex tissue, medulla tissue, or ureter tissue. In another example, an identified tissue target may be classified as normal tissue or abnormal tissue (e.g., cancerous tissue). In yet another example, an identified tissue target may be classified as treatment area (e.g., tumor or polyp intended for removal) or a non-treatment area (e.g., blood vessels, muscle, etc.). Spectral features extracted from the reflectance spectrum of the target structure may be used to categorize the target structure as a particular calculus type, or a particular tissue type, as described above with reference to FIGS. 2 and 3A-3B.

At 1150, a control signal may be generated to operate a laser system in an operating mode based on the identification of the target, such as using the laser controller 260. The operating mode may include delivery or withhold delivery of the laser beam, or a laser parameter setting for the laser system. In an example, the laser system may operate in a first operating mode if the target is identified as a calculus structure, a second operating mode if the target is identified as an anatomical structure, or a third operating mode if the target is identified as neither an anatomical structure nor a calculus structure. In an example, the first operating mode may correspond to activating the laser system to deliver a laser beam programmed with a first irradiation parameter setting to ablate or dust the identified calculi, such as kidney stones. In an example, the second operating mode may correspond to withholding the delivery of laser energy to the identified tissue, or delivering a laser beam programmed with a second irradiation parameter setting, different from the first irradiation parameter setting, to treat the identified tissue. In an example, the third operating mode may correspond to deactivating the laser system from delivery of laser energy. Examples of the laser irradiation parameters may include wavelength, power, power density, pulse parameters (e.g., pulse width, pulse rate, amplitude, duty cycle), exposure time, total dose or energy, among others.

In some examples, irradiation parameter settings may be determined respectively for a plurality of calculi types and/or for a plurality of tissue types. A calculi type-irradiation parameter setting correspondence, or a tissue type-irradiation parameter setting correspondence, may be created and stored in the memory 250, such as in a lookup table, an associative array, or the like. The laser controller 260 may use one of such stored correspondence to determine an irradiation parameter setting that corresponds to the classified calculus type or the classified tissue type.

In some examples, determination of the operating mode of the laser system may be further based on a distance 660 between the target structure and a distal end of the optical pathway, such as between the distal end of the laser fiber 512 and the target structure 122, as shown in FIGS. 6-7, or between the distal end of the optical pathway 816 for receiving and transmitting the reflected signal and the target structure 122, as shown in FIGS. 8-9. The distance 660 may be calculated using a spectroscopic property, such as a reflectance spectrum. Additionally, in some example, the measured outer diameter of the fiber or optical pathway and its angle of protrusion, and/or input signals from the endoscopic image processor, may be used to calculate the distance 660.

Figure 12:
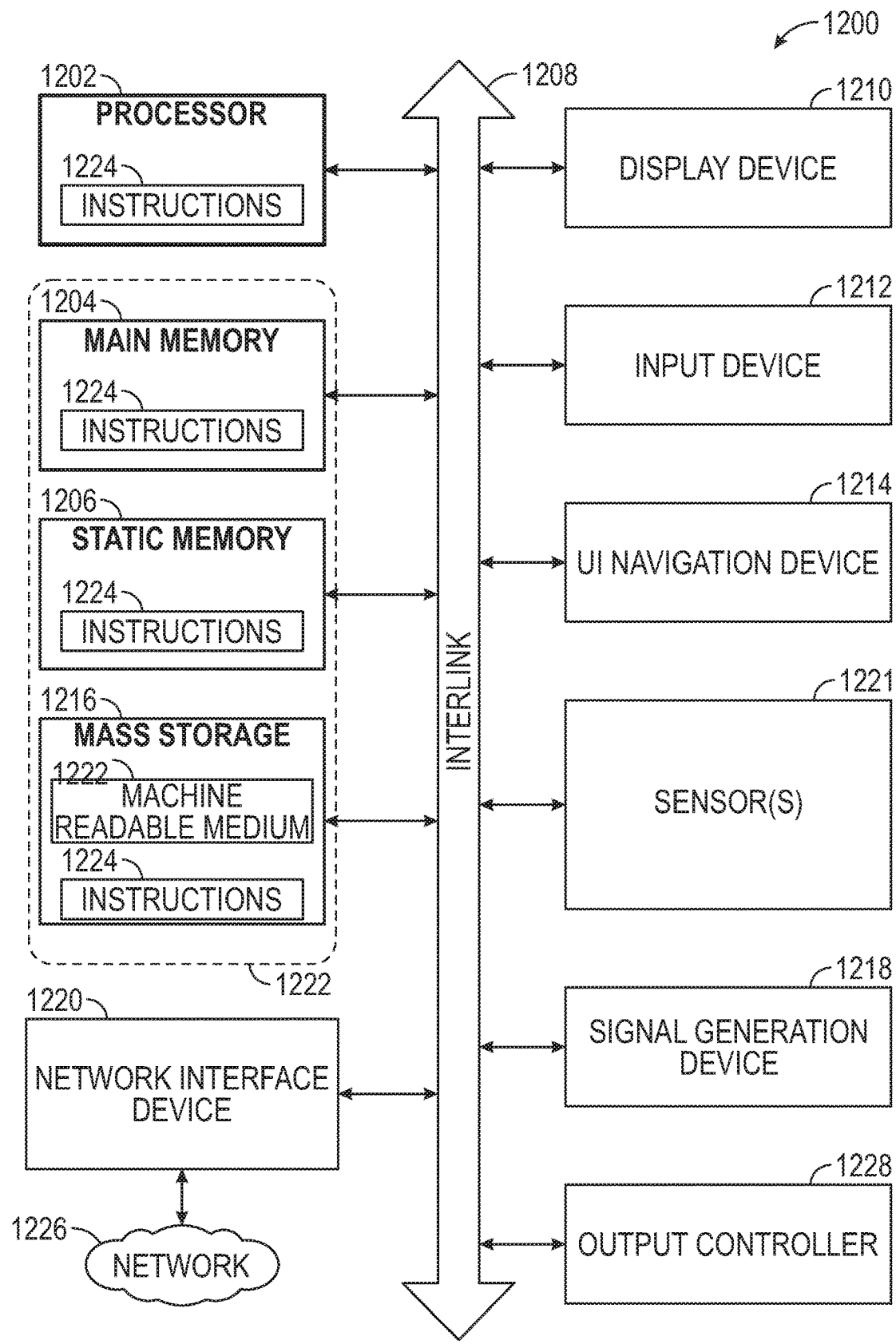
FIG. 12 is a block diagram illustrating an example machine upon which any one or more of the techniques (e.g., methodologies) discussed herein may perform.

The laser system may be controlled to deliver laser beams to the target structure if the distance 660 satisfies a condition, such as falling below a threshold or within a specified laser firing range. In an example, if the target structure is identified as an intended treatment structure type (e.g., a specified soft tissue type or a specified calculus type) but the target structure is not within the range of the laser (e.g. $d > d_{th}$), a control signal may be produced to "lock" the laser source and prevent it from firing at the target. Information about the distance 660 and that the target structure being out of the range of laser ($d > d_{th}$) may be presented to the practitioner, who may then adjust the endoscope, such as to reposition the distal end of the laser fiber. The distance 660, as well as the target structure type, may be monitored continuously and presented to the practitioner. When the target is recognized as the intended treatment structure type, and is within the range of laser ($d <= d_{th}$), a control signal may be produced to "unlock" the laser source to aim and fire laser beams at the target structure in accordance with the laser operating mode (e.g., power setting). The distance 660 may be calculated using a pre-generated calibration curve that represents a relationship between a spectroscopic reflected signal intensity and the distance 660 between a distal end of a fiber and a target structure, such as described above with reference to FIG. 10, FIG. 12 illustrates generally a block diagram of an example machine 1200 upon which any one or more of the techniques (e.g., methodologies) discussed herein may perform. Portions of this description may apply to the computing framework of various portions of the laser treatment system 100 (e.g., the laser feedback control system 101), the laser feedback control system 200, or control circuitry integrated into an endoscope such as endoscope 400.

In alternative embodiments, the machine 1200 may operate as a standalone device or may be connected (e.g., networked) to other machines. In a networked deployment, the machine 1200 may operate in the capacity of a server machine, a client machine, or both in server-client network environments. In an example, the machine 1200 may act as a peer machine in peer-to-peer (P2P) (or other distributed) network environment. The machine 1200 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1200 may include a hardware processor 1202 (e.g., a central processing unit (CPU), a graphics processing unit (GPU), a hardware processor core, or any combination thereof), a main memory 1204 and a static memory 1206, some or all of which may communicate with each other via an interlink (e.g., bus) 1208. The machine 1200 may further include a display unit 1210 (e.g., a raster display, vector display, holographic display, etc.), an alphanumeric input device 1212. (e.g., a keyboard), and a user interface (UI) navigation device 1214 (e.g., a mouse). In an example, the display unit 1210, input device 1212 and UI navigation device 1214 may be a touch screen display. The machine 1200 may additionally include a storage device (e.g., drive unit) 1216, a signal generation device 1218 (e.g., a speaker), a network interface device 1220, and one or more sensors 1221, such as a global positioning system (GPS) sensor, compass, accelerometer, or other sensors. The machine 1200 may include an output controller 1228, such as a serial (e.g., universal serial bus (USB), parallel, or other wired or wireless (e.g., infrared (IR), near field communication (NEC), etc.) connection to communicate or control one or more peripheral devices (e.g., a printer, card reader, etc.).

The storage device 1216 may include a machine readable medium 1222 on which is stored one or more sets of data structures or instructions 1224 (e.g., software) embodying or utilized by any one or more of the techniques or functions described herein. The instructions 1224 may also reside, completely or at least partially, within the main memory 1204, within static memory 1206, or within the hardware processor 1202 during execution thereof by the machine 1200. In an example, one or any combination of the hardware processor 1202, the main memory 1204, the static memory 1206, or the storage device 1216 may constitute machine readable media.

While the machine-readable medium 1222 is illustrated as a single medium, the term "machine readable medium" may include a single medium or multiple media (e.g., a centralized or distributed database, and/or associated caches and servers) configured to store the one or more instructions 1224.

The term "machine readable medium" may include any medium that is capable of storing, encoding, or carrying instructions for execution by the machine 1200 and that cause the machine 1200 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 1224 may further be transmitted or received over a communication network 1226 using a transmission medium via the network interface device 1220 utilizing any one of a number of transfer protocols (e.g., frame relay, internee protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1220 may include one or more physical jacks (e.g., Ethernet, coaxial, or phone jacks) or one or more antennas to connect to the communication network 1226. In an example, the network interface device 1220 may include a plurality of antennas to wirelessly communicate using at least one of single-input multiple-output (SIMO), multiple-input multiple-output (HMO), or multiple-input single-output (MISO) techniques. The term "transmission medium" shall be taken to include any intangible medium that is capable of storing, encoding or carrying instructions for execution by the machine 1200, and includes digital or analog communications signals or other intangible medium to facilitate communication of such software.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including"

and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A laser surgical system, comprising:
    a laser system comprising a laser source configured to generate laser energy and an optical fiber for directing the laser energy to a target in a body of a subject; and
    control circuitry configured to:
        receive a signal reflected from the target in response to electromagnetic radiation;
        generate one or more spectroscopic properties from the received reflected signal;
        identify, using the one or more spectroscopic properties, the target as one of a plurality of structure types with respective distinct compositions;
        generate a calibration curve indicating a relationship between (i) values of the one or more spectroscopic properties and (ii) corresponding fiber-to-target distances from a distal end of the optical fiber to an outer surface of the target, the calibration curve being generated based on a normalized rate of change in one or more spectroscopic properties over a known amount of change in fiber-to-target distance normalized by the generated one or more spectroscopic properties;
        determine a fiber-to-target distance between the outer surface of the target and the distal end of the optical fiber using the calibration curve and the generated one or more spectroscopic properties, wherein to determine the fiber-to-target distance, the control circuitry is configured to:
            measure respective spectroscopic property values from the received reflected signal at two distinct fiber-to-target distances;
            determine a normalized slope of the received reflected signal using a ratio of a difference between the measured spectroscopic property values to a difference between the two distinct fiber-to-target distances, the ratio being normalized to an average of the measured spectroscopic property values; and
            determine the fiber-to-target distance based on a comparison between the normalized slope and the generated calibration curve;
        determine an operating mode of the laser system based on the identification of the target and the determined fiber-to-target distance;
        and generate a control signal, based at least in part on the determined operating mode, to lock or unlock the laser system to respectively disable or enable activation of the laser system.

2. The laser surgical system of claim 1, wherein the laser system is configured to generate a laser beam for delivery to the target in the body of the subject in accordance with a laser parameter setting.

3. The laser surgical system of claim 2, wherein the control circuitry is configured to:
    generate a reflectance spectrum using the received reflected signal, the reflectance spectrum representing reflectance intensities over a plurality of wavelengths; and
    generate the one or more spectroscopic properties including extracting from the reflectance spectrum one or more spectral features including:
    a reflectance intensity at a specific wavelength;
    a statistical feature of reflectance over two or more different wavelengths; or
    a graphical feature of a graphical representation of the reflectance spectrum.

4. The laser surgical system of claim 3, wherein the control circuitry is configured to identify the target as one of a calculus structure or an anatomical structure using the one or more spectroscopic properties.

5. The laser surgical system of claim 3, wherein the control circuitry is configured to:
    classify the target as one of a plurality of calculi types with respective distinct compositions using the one or more spectroscopic properties;
    adjust a laser parameter setting for the laser system based on the classified calculus type of the target; and
    generate a control signal to the laser system to deliver a laser beam to the target of the classified calculus type in accordance with the adjusted laser parameter setting.

6. The laser surgical system of claim 5, wherein the control circuitry is configured to classify the target as one of renal calculi types including at least one of:
    a calcium phosphate (CaP) stone;
    a magnesium ammonium phosphate (MAP) stone;
    a monohydrate calcium oxalate (COM) stone;
    a cholesterol-based stone;
    a dihydrate calcium oxalate (COD) stone; or
    a uric acid (UA) stone.

7. The laser surgical system of claim 3, wherein the control circuitry is configured to:
    classify the target as one of a plurality of tissue types using the one or more spectroscopic properties; and
    determine the operating mode of the laser system based on the classified tissue type of the target.

8. The laser surgical system of claim 7, wherein the control circuitry is configured to:
    classify the target as a treatment area or a non-treatment area using the one or more spectroscopic properties; and generate a control signal to the laser system to deliver a laser beam to the treatment area, and to withhold delivery of a laser beam to the non-treatment area.

9. The laser surgical system of claim 7, wherein the control circuitry is configured to:
classify the target as normal tissue or cancerous tissue using the one or more spectroscopic properties; and
generate a control signal to the laser system to deliver a laser beam to the target of the classified cancerous tissue, and to withhold delivery of a laser beam if the target is classified as normal tissue.

10. The laser surgical system of claim 1, wherein the control circuitry is configured to determine the operating mode of the laser system including one of a first operating mode if the target is identified as a calculus structure, a second operating mode if the target is identified as an anatomical structure, or a third operating mode if the target is identified as neither an anatomical structure nor a calculus structure.

11. The laser surgical system of claim 2, comprising an endoscope coupled to the laser system, the endoscope including the control circuitry and at least one optical fiber configured to transmit one or more of the laser energy, the signal reflected from the target, or the electromagnetic radiation.

12. The laser surgical system of claim 11, wherein the at least one optical fiber includes a first optical fiber configured to transmit the signal reflected from the target to a spectroscopic sensor coupled to the control system.

13. The laser surgical system of claim 12, wherein the first optical fiber is further configured to transmit the laser energy to the target.

14. The laser surgical system of claim 12, wherein the first optical fiber is further configured to transmit the electromagnetic radiation from a light source to the target.

15. The laser surgical system of claim 12, wherein the at least one optical fiber includes a second optical fiber separate from the first optical fiber, the second optical fiber configured to transmit the laser energy to the target.

16. The laser surgical system of claim 11, wherein the control circuitry is configured to generate the one or more spectroscopic properties further using information about an outer diameter of the at least one optical fiber.

17. The laser surgical system of claim 11, wherein the control circuitry is configured to generate the one or more spectroscopic properties further using information about an angle of protrusion of a distal end of the at least one optical fiber relative to the endoscope.

18. The laser surgical system of claim 1, wherein the electromagnetic radiation produced includes one or more of:
ultraviolet waves:
visible light waves; or
infrared waves.

19. The laser surgical system of claim 1, wherein the control circuitry is coupled to a spectroscopic sensor configure to sense the signal reflected from the target in response to the electromagnetic radiation illuminating the target structure, the spectroscopic sensor including one or more of:
a Fourier Transform Infrared (FTIR) spectrometer;
a Raman spectrometer;
a UV-VIS spectrometer;
a UV-VIS-IR spectrometer; or
a fluorescent spectrometer.

20. The laser surgical system of claim 1, wherein the control circuitry is coupled to an imaging sensor configure to sense the signal reflected from the target in response to the electromagnetic radiation illuminating the target structure.

21. A method for operating a laser surgical system to deliver laser energy to a target in a body of a subject via an optical fiber, the method comprising:
illuminating the target with electromagnetic radiation;
sensing, via a spectroscopic sensor coupled a control system, a signal reflected from the target in response to the electromagnetic radiation;
generating, via the control system, one or more spectroscopic properties using the sensed reflected signal;
identifying, via the control system, the target as one of a plurality of structure types with respective distinct compositions using the one or more spectroscopic properties;
generating, via the control system, a calibration curve indicating a relationship between (i) values of the one or more spectroscopic properties and (ii) corresponding fiber-to-target distances from a distal end of the optical fiber to an outer surface of the target, the calibration curve being generated based on a normalized rate of change in one or more spectroscopic properties over a known amount of change in fiber-to-target distance normalized by the generated one or more spectroscopic properties;
determining, via the control system, a fiber-to-target distance between the outer surface of the target and the distal end of the optical fiber using the calibration curve and the generated one or more spectroscopic properties, wherein determining the fiber-to-target distance includes:
measuring respective spectroscopic property values from the sensed reflected signal at two distinct fiber-to-target distances;
determining a normalized slope of the sensed signal using a ratio of a difference between the measured spectroscopic property values to a difference between the two distinct fiber-to-target distances, the ratio being normalized to an average of the measured spectroscopic property values; and
determining the fiber-to-target distance based on a comparison between the normalized slope and the generated calibration curve;
determining an operating mode of a laser system based on the identification of the target and the determined fiber-to-target distance; and
generating, via the control system, a control signal to lock or unlock a laser system to respectively disable or enable activation of the laser system based at least in part on the determined operating mode.

22. The method of claim 21, further comprising generating a control signal to adjust a laser parameter setting for the laser system.

23. The method of claim 21, comprising generating a reflectance spectrum using the sensed reflected signal, the reflectance spectrum representing reflectance intensities over a plurality of wavelengths, and wherein generating one or more spectroscopic properties includes extracting from the reflectance spectrum one or more spectral features including:
a reflectance intensity at a specific wavelength;
a statistical feature of reflectance over two or more different wavelengths; or
a graphical feature of a graphical representation of the reflectance spectrum.

24. The method of claim 22, further comprising:
classifying the target as one of a plurality of calculi types with respective distinct compositions using the one or more spectroscopic properties;
adjusting a laser parameter setting for the laser system based on the classified calculus type of the target; and
generating a control signal to the laser system to deliver a laser beam to the target of the classified calculus type in accordance with the adjusted laser parameter setting.

25. The method of claim 22, further comprising:
classifying the target as one of a plurality of tissue types using the one or more spectroscopic properties; and
determining an operating mode of the laser system based on the classified tissue type of the target.

26. The method of claim 25, comprising:
classifying the target as a treatment area or a non-treatment area using the one or more spectroscopic properties; and
generating a control signal to the laser system to deliver a laser beam to the treatment area, and to withhold delivery of a laser beam to the non-treatment area.

27. The method of claim 25, comprising:
classifying the target as normal tissue or cancerous tissue using the one or more spectroscopic properties; and
generating a control signal to the laser system to deliver a laser beam to the target of the classified cancerous tissue, and to withhold delivery of a laser beam if the target is classified as normal tissue.

28. The method of claim 22, wherein determining the operating mode of the laser system includes one of a first operating mode if the target is identified as a calculus structure, a second operating mode if the target is identified as an anatomical structure, or a third operating mode if the target is identified as neither an anatomical structure nor a calculus structure.

29. The method of claim 22, wherein generating the one or more spectroscopic properties includes using geometry and positioning information about at least one optical fiber associated with an endoscope and configured to transmit one or more of the laser energy, the signal reflected from the target, or the electromagnetic radiation,
wherein the geometry and positioning information includes at least one of an outer diameter of the at least one optical fiber, or an angle of protrusion of a distal end of the at least one optical fiber relative to the endoscope.

30. At least one non-transitory machine-readable storage medium that includes instructions that, when executed by one or more processors of a machine, cause the machine to perform operations comprising:
illuminating a target in a body of a subject with electromagnetic radiation;
receiving a signal reflected from the target in response to the electromagnetic radiation;
generating one or more spectroscopic properties using the reflected signal;
identifying, using the one or more spectroscopic properties, the target as one of a plurality of structure types with respective distinct compositions;
generating a calibration curve indicating a relationship between (i) values of the one or more spectroscopic properties and (ii) corresponding fiber-to-target distances from a distal end of an optical fiber to an outer surface of the target, the calibration curve being generated based on a normalized rate of change in one or more spectroscopic properties over a known amount of change in fiber-to-target distance normalized by the generated one or more spectroscopic properties;
determining a fiber-to-target distance between the target and the outer surface of the distal end of the optical fiber using the calibration curve and the generated one or more spectroscopic properties, wherein the operation of determining the fiber-to-target distance includes:
measuring respective spectroscopic property values from the received reflected signal at two distinct fiber-to-target distances;
determining a normalized slope of the received reflected signal using a ratio of a difference between the measured spectroscopic property values to a difference between the two distinct fiber-to-target distances, the ratio being normalized to an average of the measured spectroscopic property values; and
determining the fiber-to-target distance based on a comparison between the normalized slope and the generated calibration curve;
based on the identification of the target and the determined fiber-to-target distance, determining an operating mode of a laser system for generating laser energy for delivery to the target; and
generating a control signal to lock or unlock the laser system to respectively disable or enable activation of the laser system based at least in part on the determined operating mode.

31. The at least one non-transitory machine-readable storage medium of claim 30, wherein the instructions cause the machine to perform operations further comprising generating a control signal to adjust a laser parameter setting for the laser system.

32. The at least one non-transitory machine-readable storage medium of claim 30, wherein the instructions cause the machine to perform operations further comprising generating, using the received reflected signal, a reflectance spectrum representing reflectance intensities over a plurality of wavelengths, and
wherein the operation of generating one or more spectroscopic properties includes extracting from the reflectance spectrum one or more spectral features including:
a reflectance intensity at a specific wavelength;
a statistical feature of reflectance over two or more different wavelengths; or
a graphical feature of a graphical representation of the reflectance spectrum.

33. The at least one non-transitory machine-readable storage medium of claim 30, wherein the operation of identifying the target as one of a plurality of structure types includes identifying the target as one of a calculus structure or an anatomical structure using the one or more spectroscopic properties.

34. The at least one non-transitory machine-readable storage medium of claim 30, wherein the instructions cause the machine to perform operations further comprising:
classifying the target as one of a plurality of calculi types with respective distinct compositions using the one or more spectroscopic properties;
adjusting a laser parameter setting for the laser system based on the classified calculus type of the target; and
generating a control signal to the laser system to deliver a laser beam to the target of the classified calculus type in accordance with the adjusted laser parameter setting.

35. The at least one non-transitory machine-readable storage medium of claim 30, wherein the instructions cause the machine to perform operations further comprising:

classifying the target as one of a plurality of tissue types using the one or more spectroscopic properties; and determining an operating mode of the laser system based on the classified tissue type of the target.

36. The at least one non-transitory machine-readable storage medium of claim 30, wherein the operation of generating the one or more spectroscopic properties includes using geometry and positioning information about at least one optical fiber associated with an endoscope and configured to transmit one or more of the laser energy, the signal reflected from the target, or the electromagnetic radiation, the geometry and positioning information including at least one of an outer diameter of the at least one optical fiber, or an angle of protrusion of a distal end of the at least one optical fiber relative to the endoscope.

* * * * *

UNITED STATES PATENT AND TRADEMARK OFFICE
CERTIFICATE OF CORRECTION

| | | |
|---|---|---|
| PATENT NO. | : 12,023,097 B2 | Page 1 of 1 |
| APPLICATION NO. | : 16/984414 | |
| DATED | : July 2, 2024 | |
| INVENTOR(S) | : Bukesov et al. | |

It is certified that error appears in the above-identified patent and that said Letters Patent is hereby corrected as shown below:

In the Claims

In Column 34, Line 9, in Claim 1, after "distance;", insert --and--

In Column 34, Line 10, in Claim 1, before "generate", delete "and"

Signed and Sealed this
Fifth Day of August, 2025

Coke Morgan Stewart
*Acting Director of the United States Patent and Trademark Office*